(12) United States Patent
Hoeltje et al.

(10) Patent No.: US 7,262,184 B2
(45) Date of Patent: Aug. 28, 2007

(54) AMIDOMETHYL-SUBSTITUTED 1-(CARBOXYALKYL)CYCLOPENTYL-CARBONYLAMINO-BENZAZEPINE-N-ACETIC ACID COMPOUNDS, PROCESS AND INTERMEDIATE PRODUCTS FOR THEIR PREPARATION AND PHARMACEUTICAL COMPOSITIONS CONTAINING THEM

(75) Inventors: Dagmar Hoeltje, Gehrden (DE); Yvan Fischer, Barsinghausen (DE); Dieter Ziegler, Hemmingen (DE); Michael Weske, Burgdorf (DE); Katrin Michaelis, Hannover (DE); Yasmin Karimi-Nejad, Hannover (DE); Josef Messinger, Sehnde (DE); Axel Pahl, Lindwedel (DE); Constanze Hoefer, Hannover (DE); Hrissanthi Ikonomidou, Berlin (DE); Lechoslaw Turski, Berlin (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 80 days.

(21) Appl. No.: 10/948,843

(22) Filed: Sep. 24, 2004

(65) Prior Publication Data
US 2005/0119247 A1   Jun. 2, 2005

Related U.S. Application Data

(60) Provisional application No. 60/530,990, filed on Dec. 22, 2003, provisional application No. 60/535,505, filed on Jan. 12, 2004.

(30) Foreign Application Priority Data
Sep. 26, 2003 (DE) .............................. 103 44 848

(51) Int. Cl.
*C07D 223/16* (2006.01)
*A61P 9/12* (2006.01)
*A61K 38/05* (2006.01)
(52) U.S. Cl. .................. 514/212.07; 540/523
(58) Field of Classification Search .......... 540/523; 514/212.07
See application file for complete search history.

(56) References Cited

U.S. PATENT DOCUMENTS

| 5,677,297 | A | 10/1997 | Waldeck et al. |
| 5,952,327 | A | 9/1999 | Waldeck et al. |
| 2003/0045449 | A1 | 3/2003 | Lowe, III et al. |

FOREIGN PATENT DOCUMENTS

| EP | 0 733 642 A1 | 9/1996 |
| EP | 0 830 863 A1 | 3/1998 |
| EP | 1 097 719 A1 | 5/2001 |
| WO | WO99/55726 | 11/1999 |
| WO | WO 00/48601 | 8/2000 |
| WO | WO 01/03699 A1 | 1/2001 |
| WO | WO 01/36610 A1 | 5/2001 |
| WO | WO 02/06492 A1 | 1/2002 |
| WO | WO 02/079143 A1 | 10/2002 |
| WO | WO 02/094176 A2 | 11/2002 |

OTHER PUBLICATIONS

Alexandru E. Benet, M.D., et al., Male Erectile Dysfunction Assessment and Treatment Options, Comprehensive Therapy 1994; 20 (12):669-673, Bronx, New York.
SR Leiblum, Definition and classification of female sexual disorders, International Journal of Impotence Research (1998), 10, Suppl. 2, S104-S106, Piscataway, NJ.
Arnold Melman et al., The Epidemiology and Pathophysiology of Erectile Dysfunction, The Journal of Urology, vol. 161, pp. 5-11, Jan. 1999, United Kingdom.
K. Park et al., Vasculogenic female sexual dysfunction: The hemodynamic basis for vaginal engorgement insufficiency and clitoral erectile insufficiency, International Journal of Impotence Research, (1997) 9, pp. 27-37, Boston, MA.
Makoto Sumitomo et al., Chemosensitization of Androgen-Independent Prostate Cancer with Neutral Endopeptidase, vol. 10, pp. 260-266, Jan. 1, 2004, New York, NY.
Herbert M. User et al., Microarray Analysis and Description of SMR1 Gene in Rat Penis in a Post-Radical Prostatectomy Model of Erectile Dysfunction, The Journal of Urology, vol. 170, pp. 298-801, Jul. 2003, Chicago, Illinois.
Jennifer R. Berman et al., Female sexual dysfunction: anatomy, physiology, evaluation and treatment options; Current Opinion in Urology, 1999, 9:563-568, Boston, MA.

(Continued)

Primary Examiner—Bruck Kifle
(74) Attorney, Agent, or Firm—Crowell & Moring LLP

(57) ABSTRACT

Compounds having neutral endopeptidase (NEP) and/or human soluble endopeptidase (hSEP) inhibitory activity corresponding to the formula 1,

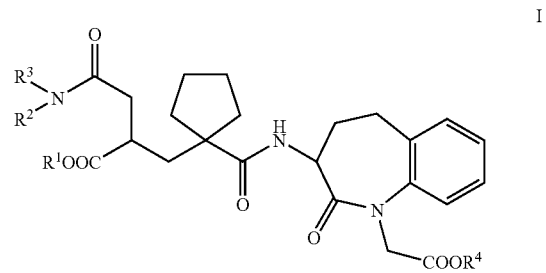

wherein the substituents $R^1$, $R^2$, $R^3$ and $R^4$ have the meanings given in the description and also pharmaceutical compositions containing these compounds, in particular pharmaceutical compositions suitable for treating or inhibiting cardiovascular diseases, sexual dysfunction and/or adverse conditions associated with apoptosis.

14 Claims, No Drawings

OTHER PUBLICATIONS

I. Goldstein et al., Vasculogenic female sexual dysfunction: vaginal engorgement and clitoral erectile insufficiency syndromes, International Journal of Impotence Research (1998) 10, Suppl. 2, S84-S90, Boston, MA.

A.M. Naylor, Endogenous neurotransmitters mediating penile erection, British Journal of Urology (1998), 81, pp. 424-431, Sandwich, UK.

Reza Tabrizchi, SLV-306 Solvay, Current Opinion in Investigational Drugs, 2003, vol. 4, No. (3), 329-332, Canada.

Harvey C. Taub, M.D. et al., Relationship Between Contraction and Relaxation in Human and Rabbit Corpus Cavernosum, Adult Urology, Dec. 1993, vol. 42, No. 6, pp. 698-704, Bronx, New York.

Keiji Kubo et al., Nonpeptide Angiotensin II Receptor Antagonists. Synthesis and Biological Activity of Potential Prodrugs of Benzimidazole-7-carboxylic Acids, J. Med. Chem. 1998, 36, pp. 2343-2349, Osaka, Japan.

Luis M. Cruz-Orive et al., Recent stereological methods for cell biology: a brief survey, Am. J. Physiol. 258 (Lung Cell. Mol. Physiol. 2): L148-L156, 1990, Switzerland.

R. J. Levin, VIP, Vagina, Clitoral and Perurethral Glans—an Update on Human Female Genital Arousal, Exp. Clin. Endocrinol., vol. 98, No. 2, 1991, pp. 61-69, Great Britain.

Jama, Impotence, NIH Consensus Conference, Jul. 7, 1993, vol. 270, No. 1, pp. 83-90, Bethesda, MD.

F. W. Sum et al., Prodrugs of CL316243: A Selective $\beta_3$-Adrenergic Receptor Agonist for Treating Obesity and Diabetes, Bioorganic & Medicinal Chemistry Letters 9 (1999) pp. 1921-1926, Pearl River, NY.

Yoshinobu Yoshimura et al., Preparation of 1-Acyloxyethyl Esters of 7-[2-(2-Aminothiazol-4-YL)Acetamidol]-3-[[[1-(2-Dimethylaminoethyl)-1$H$-Tetrazol-5-YL]Thio]-Methyl]Ceph-3-EM-4-Carboxylic Acid (Cefotiam) and Their Oral Absorption In Mice, The Journal of Antibiotics, vol. XXXIX No. 9, pp. 1329-1342, Osaka, Japan.

AMIDOMETHYL-SUBSTITUTED 1-(CARBOXYALKYL) CYCLOPENTYL-CARBONYLAMINO-BENZAZEPINE-N-ACETIC ACID COMPOUNDS, PROCESS AND INTERMEDIATE PRODUCTS FOR THEIR PREPARATION AND PHARMACEUTICAL COMPOSITIONS CONTAINING THEM

BACKGROUND OF THE INVENTION

The present invention relates to novel amidomethyl-substituted 1-(carboxyalkyl)-cyclopentylcarbonylamino-benzazepine-N-acetic acid derivatives which are useful e.g. for the prophylaxis and/or treatment of cardiovascular conditions or diseases, especially cardiac insufficiency, in particular congestive heart failure; hypertension, including secondary forms of hypertension such as essential hypertension, renal hypertension and/or pulmonary hypertension and/or for the prophylaxis and/or treatment of sexual dysfunction and/or for the prophylaxis and/or treatment of adverse conditions associated with apoptosis, and also to medicaments containing these compounds. Furthermore, the invention relates to a process for the preparation of the novel amidomethyl-substituted benzazepine-N-acetic acid derivatives and intermediate products of this process.

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes selfesteem and disrupts personal relationships thereby inducing personal distress.

Apoptosis is closely involved in morphogenesis and histogenesis in the development process, maintenance of homeostasis, and bio-defense, and it is cell death having an important role in maintaining individual lives. When the death process regulated by genes is congenially or postnatally hindered, apoptosis is excessively induced or inhibited to cause functional disorders in various organs, and thus diseases. Drugs showing an apoptosis inhibitory activity can be used as agents for the prophylaxis and treatment of diseases which are thought to be mediated by promotion of apoptosis.

Cardiovascular-active benzazepine-, benzoxazepine- and benzothiazepine-N-acetic acid derivatives having a marked inhibitory action on the enzyme neutral endopeptidase (=NEP) are already known from specification EP 0 733 642 A1 (=U.S. Pat. No. 5,677,297). In addition, the compounds described therein also have lesser properties which inhibit endothelin-converting enzyme (=ECE). Further favourable pharmacological properties of compounds falling within the structural scope of EP 0 733 642 A1 are known from documents EP 0 830 863 A1 (=U.S. Pat. No. 5,783,53), WO 00/48601 A1 (=U.S. Pat. No. 6,482,820) and WO 01/03699 A1 (=US-2003-0040512-A1).

Phosphonic acid substituted benzazepinone-N-acidic acid derivatives with a combined inhibitory effect on NEP and ECE are disclosed in document EP 0 916 679 A1 (=U.S. Pat. No. 5,952,327).

Pharmaceutical preparations are known from specification WO 02/094176 A2 which contain compounds having an advantageous combinatory action which inhibits the metalloprotease enzymes NEP and IGS5 and have, inter alia, cardiovascular-active properties. Suitable compounds for such combination preparations are also compounds which fall within the scope of specifications EP 0 733 642 A1 and EP 0 916 679 A1. The enzyme IGS5, as it is to be understood in the context of this invention, and its physiological role in connection with cardiovascular diseases, is known per se from the specification WO 01/36610 A1. The aforementioned enzyme IGS5 is also known as "human soluble endopeptidase" (=hSEP).

International application no. WO 99/55726 A1 discloses that certain thiol inhibitors of ECE are useful among other things for treating or inhibiting erectile dysfunction.

European patent application no. EP 1 097 719 A1 discloses the use of NEP inhibitors for the treatment of female sexual dysfunction (=FSD).

Publication WO 02/06492 A1 discloses i.a. antibodies against and inhibitors of a specific polypeptide having soluble secreted endopeptidase (=SEP) activity.

Published U.S. patent application no. US 2003-0045449 discloses that matrix-metalloprotease inhibitors are useful for the treatment of neurodegenerative diseases. Problems associated with that invention are first that matrix-metalloprotease inhibitors comprise a broad group of protease inhibitors, and second that according to the said application the metalloproteases must be used in a pharmaceutical composition also containing an N-NOS inhibitor.

Published U.S. patent application no. US 2002-0013307 teaches the use of vasopeptidase inhibitors to treat or slow the progression of cognitive dysfunction and to treat and/or prevent dementia.

M. Sumitomo et al. (see Clinical Cancer Research 10 (2004) 260-266) describe the chemosensitization of androgen-independent prostate cancer with NEP.

SUMMARY OF THE INVENTION

It was an object of the present invention to provide novel active substances having a combined activity profile inhibiting the enzymes NEP, hSEP and ECE.

Another object of the invention was to provide active substances which are suitable for the prophylaxis and/or treatment of cardiovascular conditions or diseases, especially cardiac insufficiency, in particular congestive heart failure; hypertension, including secondary forms of hypertension such as essential hypertension, renal hypertension and/or pulmonary hypertension.

A further object of the invention was to provide active substances which are useful for inhibiting or treating sexual dysfunction.

An additional object of the invention was to provide active substances which are useful in inhibiting or treating adverse conditions associated with apoptosis.

These and other objects have been achieved in accordance with the present invention by providing a compound corresponding to the formula I:

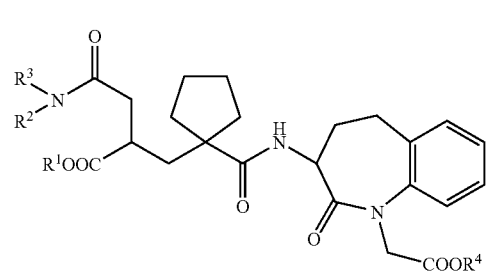

wherein

R¹ is hydrogen or a group forming a biolabile ester,

R² is hydrogen, $C_{1-4}$-alkyl or $C_{1-4}$-hydroxyalkyl, the hydroxyl group of which is optionally esterified with $C_{2-4}$-alkanoyl or an amino acid residue, and R³ is $C_{1-4}$-alkyl; $C_{1-4}$-alkoxy-$C_{1-4}$-alkyl; $C_{1-4}$-hydroxyalkyl, which is optionally substituted by a second hydroxyl group and the hydroxyl groups of which are each optionally esterified with $C_{2-4}$-alkanoyl or an amino acid residue; $(C_{0-4}$-alkyl$)_2$amino-$C_{1-6}$-alkyl; $C_{3-7}$-cycloalkyl; $C_{3-7}$-cycloalkyl-$C_{1-4}$-alkyl; phenyl-$C_{1-4}$-alkyl, the phenyl group of which is optionally substituted once or twice by $C_{1-4}$-alkyl, $C_{1-4}$-alkoxy or halogen; naphthyl-$C_{1-4}$-alkyl; $C_{3-6}$-oxoalkyl; phenylcarbonylmethyl, the phenyl group of which is optionally substituted once or twice by $C_{1-4}$-alkyl, $C_{1-4}$-alkoxy or halogen, or 2-oxoazepanyl, or R² and R³ together are $C_{4-7}$-alkylene, the methylene groups of which are optionally replaced once or twice by carbonyl, nitrogen, oxygen or sulphur, or which are optionally substituted once by hydroxy, which is optionally esterified with $C_{2-4}$-alkanoyl or an amino acid residue; $C_{1-4}$-alkyl; $C_{1-4}$-hydroxyalkyl, the hydroxyl group of which is optionally esterified with $C_{2-4}$-alkanoyl or an amino acid residue; phenyl or benzyl, and R⁴ is hydrogen or a group forming a biolabile ester, or a physiologically acceptable salt thereof.

It has now surprisingly been found that a group according to the invention of novel amidomethyl-substituted 1-(carboxyalkyl)-cyclopentylcarbonylamino-benzazepine-N-acetic acid derivatives is distinguished by an action profile which inhibits the enzymes NEP and hSEP, and to a certain extent also ECE, and therefore appears suitable for the prophylaxis and/or treatment of cardiovascular conditions or diseases, especially cardiac insufficiency, in particular congestive heart failure; hypertension, including secondary forms of hypertension such as essential hypertension, renal hypertension and/or pulmonary hypertension; and/or or for the prophylaxis and/or treatment of sexual dysfunction and/or for the prophylaxis and/or treatment of adverse conditions associated with apoptosis.

The invention thus relates to novel amidomethyl-substituted 1-(carboxyalkyl)-cyclopentylcarbonylamino-benzazepine-N-acetic acid derivatives of the general formula I,

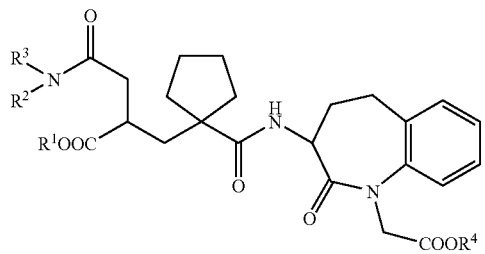

I wherein

R¹ is hydrogen or a group forming a biolabile ester,

R² is hydrogen, $C_{1-4}$-alkyl or $C_{1-4}$-hydroxyalkyl, the hydroxyl group of which is optionally esterified with $C_{2-4}$-alkanoyl or an amino acid residue, and R³ is $C_{1-4}$-alkyl; $C_{1-4}$-alkoxy-$C_{1-4}$-alkyl; $C_{1-4}$-hydroxyalkyl, which is optionally substituted by a second hydroxyl group and the hydroxyl groups of which are each optionally esterified with $C_{2-4}$-alkanoyl or an amino acid residue; $(C_{0-4}$-alkyl$)_2$amino-$C_{1-4}$-alkyl; $C_{3-7}$-cycloalkyl; $C_{3-7}$-cycloalkyl-$C_{1-4}$-alkyl; phenyl-$C_{1-4}$-alkyl, the phenyl group of which is optionally substituted 1-2 times by $C_{1-4}$-alkyl, $C_{1-4}$-alkoxy and/or halogen; naphthyl-$C_{1-4}$-alkyl; $C_{3-6}$-oxoalkyl; phenylcarbonylmethyl, the phenyl group of which is optionally substituted 1-2 times by $C_{1-4}$-alkyl, $C_{1-4}$-alkoxy and/or halogen, or 2-oxoazepanyl, or R² and R³ together are $C_{4-7}$-alkylene, the methylene groups of which are optionally replaced 1-2 times by carbonyl, nitrogen, oxygen and/or sulfur and which are optionally substituted once by hydroxy, which is optionally esterified with $C_{2-4}$-alkanoyl or an amino acid residue; $C_{1-4}$-alkyl; $C_{1-4}$-hydroxyalkyl, the hydroxyl group of which is optionally esterified with $C_{2-4}$-alkanoyl or an amino acid residue; phenyl or benzyl, and R⁴ is hydrogen or a group forming a biolabile ester, and physiologically compatible salts of acids of Formula I and/or physiologically compatible acid addition salts of compounds of Formula I. Furthermore, a subject of the invention is medicaments containing the compounds of Formula I. Even further, a subject of the invention is a process for the preparation of the compounds of Formula I and intermediate products of this process.

Where in the compounds of Formula I or in other compounds described within the context of the present invention substituents are or contain $C_{1-4}$-alkyl, these may each be straight-chain or branched. Where substituents in compounds of Formula I stand for halogen, fluorine, chlorine or bromine are suitable. Chlorine is preferred. Where substituents contain $C_{2-4}$-alkanoyl, this may be straight-chain or branched. Acetyl is preferred as $C_{2-4}$-alkanoyl.

Where in the compounds of Formula I hydroxyl groups are esterified with amino acids and, these amino acids may be derived from natural or non-natural, α- or β-amino acids. Suitable amino acids which can be used are for example selected from the group consisting of alanine, 2-aminohexanoic acid (=norleucine), 2-aminopentanoic acid (=norvaline), arginine, asparagine, aspartic acid, cysteine, 3,4-dihydroxyphenylalanine (=dopa), glutamine, glutamic acid, glycine, histidine, isoleucine, leucine, lysine, methionine, ornithine (=2,5-diaminovaleric acid), 5-oxo-2-pyrrolidinecarbonic acid (=pyroglutamic acid), phenylalanine, proline, serine, threonine, thyronine, tryptophan, tyrosine and valine. Preferred are amino acid residues which are derived from alanine, asparagine, glutamine, glycine, isoleucine, leucine, lysine, ornithine, phenylalanine, proline and valine.

The compounds of Formula I represent dicarboxylic acid derivatives optionally esterified with groups forming biolabile esters. The biolabile esters of Formula I as a rule represent administerable precursors (="prodrugs") of the free acids. Then, monoesters or diesters of the compounds of Formula I may occur. Depending on the form of administration, the biolabile esters or the free acids are preferred, the latter being suitable in particular for intravenous (=i.v.) administration.

Groups which can be cleaved under physiological conditions in vivo, releasing bioavailable derivatives of the compounds of Formula I, are suitable as groups forming biolabile esters R¹ and R⁴. Suitable examples of this are $C_{1-4}$-alkyl groups, in particular methyl, ethyl, n-propyl and isopropyl; $C_{1-4}$-alkyloxy-$C_{1-4}$-alkyloxy-$C_{1-4}$-alkyl groups, in particular methoxyethoxymethyl; $C_{3-7}$-cycloalkyl groups, in particular cyclohexyl; $C_{3-7}$-cycloalkyl-$C_{1-4}$-alkyl groups, in particular cyclopropylmethyl; N,N-di-($C_{0-4}$-alkyl)amino-$C_{1-6}$-alkyl groups; phenyl or phenyl-$C_{1-4}$-alkyl groups optionally substituted in the phenyl ring once or twice by halogen, $C_{1-4}$-alkyl or $C_{1-4}$-alkoxy or by a $C_{1-4}$-alkylene chain bonded to two adjacent carbon atoms; dioxolanylmethyl groups optionally substituted in the dioxolane ring by $C_{1-4}$-alkyl; $C_{2-6}$-alkanoyloxy-$C_{1-4}$-alkyl groups optionally substituted at the oxy-$C_{1-4}$-alkyl group by $C_{1-4}$-alkyl; double esters like 1-[[($C_{1-4}$-alkyl)carbonyl]oxy]$C_{1-4}$-alkyl esters, e.g. (RS)-1-[[(isopropyl)carbonyl]oxy]ethyl or (RS)-1-[[(ethyl)carbonyl]oxy]-2-methylpropyl (for preparation see e.g. F. W. Sum et al., Bioorg. Med. Chem. Lett. 9 (1999) 1921-1926 or Y. Yoshimura et al., The Journal of Antibiotics 39/9 (1986) 1329-1342); carbonate esters like 1-[[($C_{4-7}$-cycloalkyloxy)carbonyl]oxy] $C_{1-4}$-alkyl esters, preferably (RS)-1-[[(cyclohexyloxy)carbonyl]oxy]ethyl (=cilexetil; for preparation see e.g. K. Kubo et al., J. Med. Chem. 36 (1993) 2343-2349, cited as "Kubo et al." hereinafter)) or 2-oxo-1,3-dioxolan-4-yl-$C_{1-4}$-alkyl esters which optionally contain a double bond in the dioxolan ring, preferably 5-methyl-2-oxo-1,3-dioxolen-4-yl-methyl (=medoxomil, for preparation see e.g. Kubo et al.) or 2-oxo-1,3-dioxolan-4-yl-methyl (=(methyl)ethylene-carbonate). Where the group forming a biolabile ester represents an optionally substituted phenyl-$C_{1-4}$-alkyl group, this may contain an alkylene chain with 1 to 3, preferably 1, carbon atoms and preferably stands for optionally substituted benzyl, in particular for 2-chlorobenzyl or 4-chlorobenzyl. Where the group forming a biolabile ester represents an optionally substituted phenyl group, the phenyl ring of which is substituted by a lower alkylene chain, this may contain 3 to 4, preferably 3, carbon atoms and in particular be indanyl. Where the group forming a biolabile ester represents an optionally substituted $C_{2-6}$-alkanoyloxy-$C_{1-4}$-alkyl group, the $C_{2-6}$-alkanoyl group may be straight-chain or branched.

$R^1$ preferably has the meanings hydrogen, ethyl, methoxyethoxymethyl, (RS)-1-[[(isopropyl)carbonyl]oxy]ethyl, (RS)-1-[[(ethyl)carbonyl]oxy]-2-methylpropyl, (RS)-1-[[(cyclohexyloxy)carbonyl]oxy]ethyl, 5-methyl-2-oxo-1,3-dioxolen-4-yl-methyl, 2-oxo-1,3-dioxolan-4-yl-methyl or (RS)-1-[[(ethoxy)carbonyl]oxy]ethyl.

$R^2$ preferably has the meanings hydrogen, methyl, ethyl, 2-hydroxyethyl or 3-hydroxypropyl, each hydroxyl group optionally being esterified with $C_{2-4}$-alkanoyl or an amino acid residue.

Where $R^3$ has the meaning ($C_{0-4}$-alkyl)$_2$amino-$C_{1-6}$-alkyl, one or two $C_{0-4}$-alkyl groups can independently of each other be present. More specifically, "($C_{0-4}$-alkyl)$_2$amino-$C_{1-6}$-alkyl" expressly comprises the meanings "($C_0$)$_2$-alkylamino-$C_{1-4}$-alkyl", "($C_0$)($C_{1-4}$)-alkylamino-$C_{1-6}$-alkyl" and "($C_{1-4}$)$_2$-alkylamino-$C_{1-6}$-alkyl". "($C_0$)$_2$-alkylamino-$C_{1-6}$-alkyl" is meant to denominate an unsubstituted primary (=—NH$_2$) amino group bonded to $C_{1-6}$-alkyl(ene); "($C_0$)($C_{1-4}$)-alkylamino-$C_{1-6}$-alkyl" is meant to denominate a secondary amino group monosubstituted by ($C_{1-4}$)-alkyl and bonded to $C_{1-6}$-alkyl(ene); "($C_{1-4}$)$_2$-alkylamino-$C_{1-6}$-alkyl" is meant to denominate a tertiary amino group disubstituted by ($C_{1-4}$)-alkyl and bonded to $C_{1-6}$-alkyl(ene). $R^3$ preferably has the meanings isopropyl; methoxyethyl; 2-hydroxyethyl or 3-hydroxypropyl, each hydroxyl group optionally being esterified with $C_{2-4}$-alkanoyl or an amino acid residue; 3-acetyloxy-n-propyl; cyclopropylmethyl; 2-methoxy-benzyl, 4-methoxybenzyl; 4-methoxyphenylethyl; 2,4-dimethoxybenzyl; 1-naphthylmethyl; 3-oxo-1,1-dimethylbutyl; phenyl-2-oxoethyl; 2-(4-methoxyphenyl)-2-oxoethyl; 3-(2-oxoazepanyl); ($C_{0-4}$-alkyl)$_2$amino-$C_{1-6}$-alkyl, in particular dimethylamino-n-propyl, (methyl)aminoethyl, amino-n-propyl, amino-n-butyl or amino-n-pentyl.

Where $R^2$ and $R^3$ together are $C_{4-7}$-alkylene, the methylene groups of which are optionally replaced or optionally substituted, optionally in each case morpholine; piperidine; 4-ketopiperidine; 4-hydroxypiperidine, optionally being esterified with $C_{2-4}$-alkanoyl or an amino acid residue at the hydroxyl group; piperazine or pyrrolidine is preferred.

$R^4$ preferably has the meanings hydrogen, $C_{1-4}$-alkyl, p-methoxybenzyl, N,N-di-($C_{0-4}$-alkyl)amino-$C_{1-6}$-alkyl, (RS)-1-[[(isopropyl)carbonyl]oxy]ethyl, (RS)-1-[[(ethyl)carbonyl]-oxy]-2-methylpropyl, (RS)-1-[[(cyclohexyloxy) carbonyl]oxy]ethyl, 5-methyl-2-oxo-1,3-dioxolen-4-yl-methyl, 2-oxo-1,3-dioxolan-4-yl-methyl or (RS)-1-[[(ethoxy) carbonyl]oxy]-ethyl.

Particularly preferred compounds of Formula I include compounds selected from the group consisting of:

2-{[1-({[1-(carboxymethyl)-2-oxo-2,3,4,5-tetrahydro-1H-1-benzazepin-3-yl]amino}-carbonyl)cyclopentyl]methyl}-4-[isopropyl(methyl)amino]-4-oxobutanoic acid (32);

2-{[1-({[1-(carboxymethyl)-2-oxo-2,3,4,5-tetrahydro-1H-1-benzazepin-3-yl]amino}carbonyl)cyclopentyl]methyl}-4-(dimethylamino)-4-oxobutanoic acid (54);

2-{[1-({[1-(carboxymethyl)-2-oxo-2,3,4,5-tetrahydro-1H-1-benzazepin-3-yl]amino}carbonyl)cyclopentyl]methyl}-4-(diethylamino)-4-oxobutanoic acid (55);

2-{[1-({[1-(carboxymethyl)-2-oxo-2,3,4,5-tetrahydro-1H-1-benzazepin-3-yl]amino}carbonyl)cyclopentyl]methyl}-4-[(2-hydroxyethyl)(methyl)amino]-4-oxobutanoic acid (43);

2-{[1-({[1-(carboxymethyl)-2-oxo-2,3,4,5-tetrahydro-1H-1-benzazepin-3-yl]amino}carbonyl)cyclopentyl]methyl}-4-[(3-hydroxypropyl)(methyl)amino]-4-oxobutanoic acid (56);

2-{[1-({[1-(carboxymethyl)-2-oxo-2,3,4,5-tetrahydro-1H-1-benzazepin-3-yl]amino}-carbonyl)cyclopentyl]methyl}-4-(4-hydroxypiperidin-1-yl)-4-oxobutanoic acid (57);

2-{[1-({[1-(carboxymethyl)-2-oxo-2,3,4,5-tetrahydro-1H-1-benzazepin-3-yl]amino}-carbonyl)cyclopentyl]methyl}-4-oxo-4-[4-(L-valyloxy)piperidin-1-yl]butanoic acid (68);

2-{[1-({[1-(carboxymethyl)-2-oxo-2,3,4,5-tetrahydro-1H-1-benzazepin-3-yl]amino}-carbonyl)cyclopentyl]methyl}-morpholin-4-yl-4-oxobutanoic acid (66);

2-{[1-({[1-(carboxymethyl)-2-oxo-2,3,4,5-tetrahydro-1H-1-benzazepin-3-yl]amino}-carbonyl)cyclopentyl]methyl}4-oxo-4-(4-oxopiperidin-1-yl)butanoic acid (45);

4-[bis(2-hydroxyethyl)amino]-2-{[1-({[1-(carboxymethyl)-2-oxo-2,3,4,5-tetrahydro-1H-1-benzazepin-3-yl] amino}carbonyl)cyclopentyl]methyl}-4-oxobutanoic acid (58);

2-{[1-({[1-(carboxymethyl)-2-oxo-2,3,4,5-tetrahydro-1H-1-benzazepin-3-yl]amino}carbonyl)cyclopentyl]methyl}-4-{ethyl[3-(ethylamino)propyl]amino}-4-oxobutanoic acid (52), 2-{[1-({[1-(carboxymethyl)-2-oxo-2,3,4,5-tetrahydro-1H-1-benzazepin-3-yl]amino}-carbonyl)cyclopentyl]methyl}-4-[[2-(dimethylamino)ethyl](methyl)amino]-4-oxobutanoic acid (59), 4-[(3-aminopropyl)(ethyl)amino]-2-{[1-({[1-(carboxymethyl)-2-oxo-2,3,4,5-tetrahydro-1H-1-benzazepin-3-yl] amino}carbonyl)cyclopentyl]methyl}-4-oxobutanoic acid (67);

2-{[1-({[1-(carboxymethyl)-2-oxo-2,3,4,5-tetrahydro-1H-1-benzazepin-3-yl]amino}-carbonyl)cyclopentyl]methyl}-4-{methyl[2-(methylamino)ethyl]amino}-4-oxobutanoic acid (68), 4-[(4-aminobutyl)(methyl)amino]-2-{1-({[1-(carboxymethyl)-2-oxo-2,3,4,5-tetrahydro-1H-1-benzazepin-3-yl]amino}carbonyl)cyclopentyl]methyl}-4-oxobutanoic acid (75), 4-[(4-aminobutyl)(ethyl)amino]-2-{1-({[1-(carboxymethyl)-2-oxo-2,3,4,5-tetrahydro-1H-1-benzazepin-3-yl]amino}carbonyl)cyclopentyl]methyl}-4-oxobutanoic acid (76), 2-{[1-({[1-(carboxymethyl)-2-oxo-2,3,4,5-tetrahydro-1H-1-benzazepin-3-yl]amino}-carbonyl)cyclopentyl]methyl}-4-{methyl[3-(methylamino)propyl]amino}-4-oxobutanoic acid (77), 2-[1-(1-carboxymethyl)-2-oxo-2,3,4,5-tetrahydro-1H-benzo[b]azepin-3-ylcarbamoyl)-cyclopentylmethyl]-N-(3-(dimethylamino-propyl)-N-methyl-succinamic acid (60, 64), and 4-[(5-aminopentyl)(methyl)amino]-2-{1-({[1-(carboxymethyl)-2-oxo-2,3,4,5-tetrahydro-1H-1-benzazepin-3-yl]amino}carbonyl)cyclopentyl]methyl}-4-oxobutanoic acid (78), together with their biolabile esters and physiologically compatible salts of acids of these compounds of Formula I and/or physiologically compatible acid addition salts of these compounds of Formula I.

According to the invention, the novel compounds of Formula I and their salts are obtained by reacting a compound of the general formula II,

II wherein $R^{101}$ and $R^{401}$, independently of each other, are each an acid-protecting group, with a compound of the general formula III, $$R^2-\text{NH}-R^3$$

III wherein $R^2$ and $R^3$ have the above meanings,
where $R^2$ and/or $R^3$ contain free hydroxyl groups, if desired these are reacted with a compound of the general formula IV, $$C_{1-3}-C(O)-X \qquad \text{IV}$$

wherein X stands for a leaving group, or with an amino acid derivative protected by a suitable protective group,
where $R^{101}$ and/or $R^{401}$ do not represent desired groups forming a biolabile ester and/or where $R^2$ and/or $R^3$ comprise protective groups in any present amino acid residue, these are cleaved off in succession in the resulting compounds simultaneously or individually in any desired sequence and if desired the acid functions released in each case are converted into biolabile ester groups, and if desired resulting acids of Formula I are converted into their physiologically compatible salts, or salts of the acids of Formula I are converted into the free acids and/or bases of Formula I are converted into their acid addition salts or acid addition salts are converted into free bases of Formula I.

Suitable physiologically compatible salts of acids of Formula I are in each case alkali metal, alkaline-earth metal or ammonium salts thereof, for example sodium, potassium or calcium salts thereof, physiologically compatible, pharmacologically neutral organic salts thereof with amines such as for example ammonia, diethylamine, tert. butylamine, N-methylglucamine, choline, or with amino acids such as for example arginine. Where in compounds of Formula I the substituents $R^2$ and/or $R^3$ contain basic groups, in particular nitrogen, the compounds of Formula I may also occur in the form of acid addition salts. Physiologically compatible acid addition salts of compounds of Formula I are their conventional salts with inorganic acids, for example sulfuric acid, phosphoric acid or hydrohalic acids, preferably hydrochloric acid, or with organic acids, for example lower aliphatic monocarboxylic, dicarboxylic or tricarboxylic acids such as maleic acid, fumaric acid, tartaric acid, citric acid, or with sulfonic acids, for example lower alkanesulfonic acids such as methanesulfonic acid.

Conventional protective groups for protecting carboxylic acid functions may be selected as acid-protecting groups $R^{101}$ and $R^{401}$, which can then be cleaved off again using known methods. Suitable protective groups for carboxylic acids are known, for example, from McOmie, "Protective Groups in Organic Chemistry", Plenum Press (cited as "McOmie" hereinafter), and Greene, Wuts, "Protective Groups in Organic Synthesis", Wiley Interscience Publication (cited as "Greene" hereinafter), each in the most recent edition. Groups forming a biolabile ester may also be used as acid-protecting groups. The compounds obtained upon reaction of compounds of Formula II with compounds of Formula III in these cases already represent esters of Formula I according to the invention.

Suitable acid-protecting groups $R^{101}$ and $R^{401}$ are in particular those groups which can be selectively cleaved or selectively introduced independently of each other. Examples of acid-protecting groups which are cleavable under different conditions, which may also represent groups forming biolabile esters, are: unbranched lower alkyl groups such as ethyl, which can be cleaved off relatively easily under basic conditions; branched lower alkyl groups such as tert. butyl, which can be cleaved off easily by acids such as trifluoroacetic acid; phenylmethyl groups optionally substituted in the phenyl ring such as benzyl, which can easily be cleaved off by hydrogenolysis or alternatively under basic conditions; phenylmethyl groups substituted one or more times in the phenyl ring by lower alkoxy, such as p-methoxybenzyl, which are cleaved relatively easily under oxidative conditions, for example under the action of 2,3-dichloro-5,6-dicyano-1,4-benzoquinone (=DDQ) or ceric ammonium nitrate; or the known silicon-containing protective groups which can easily be cleaved by fluoride ions. The person skilled in the art is familiar with selecting suitable protective groups to obtain a desired substitution pattern.

The compounds of Formula I contain two chiral carbon atoms, namely the carbon atom bearing the amide side chain in position 3 of the benzazepine skeleton (=$C_b$*) and the carbon atom bearing the radical "—COOR$^1$" (=$C_a$*). The compounds can thus be present in a total of four stereoisomeric forms. The present invention comprises both the mixtures of stereoisomers and enantiomers, and also the isomerically pure compounds of Formula I. Isomerically pure compounds of Formula I are preferred. Particularly preferred are compounds of Formula I wherein the carbon atom bearing the amide side chain in position 3 of the benzazepine skeleton is in the "S" configuration. With respect to the chiral carbon atom "*$C_a$" bearing the radical "—$COOR^1$", the configuration of the compounds of Formula I which is preferred according to the invention in the context of this invention is provisionally assigned the configuration designation "rel1" (see the experimental part). It can be derived by analogous observations of suitable compounds of known configuration that the preferred configuration "rel1" at the chiral center "*$C_a$" is probably likewise the "S" configuration.

The reaction of the acids of Formula II with the amines of Formula III can be carried out according to conventional methods for the formation of amide groups by aminoacylation. The carboxylic acids of Formula II or their reactive derivatives may be used as acylation agents. In particular mixed acid anhydrides and acid halides are suitable reactive derivatives. Thus for example acid chlorides or acid bromides of the acids of Formula II or mixed esters of the acids of Formula II with organic sulfonic acids, for example with lower-alkanesulfonic acids optionally substituted by halogen, such as methanesulfonic acid or trifluoromethanesulfonic acid, or with aromatic sulfonic acids such as benzenesulfonic acids or with benzenesulfonic acids substituted by lower alkyl or halogen, e.g. toluenesulfonic acids or bromobenzenesulfonic acids, can be used. The acylation may take place in an organic solvent which is inert under the reaction conditions at temperatures between −20° C. and room temperature (=RT). Suitable solvents are halogenated hydrocarbons such as dichloromethane or aromatic hydrocarbons such as benzene or toluene or cyclic ethers such as tetrahydrofuran (=THF) or dioxane or mixtures of these solvents.

The acylation can expediently, in particular if a mixed anhydride of the acids of Formula II with a sulfonic acid is used as acylation agent, be carried out in the presence of an acid-binding reagent. Suitable acid-binding agents are for example organic bases which are soluble in the reaction mixture such as tertiary nitrogen bases, for example tert.-lower alkylamines and pyridines such as triethylamine, tripropylamine, N-methylmorpholine, pyridine, 4-dimethylaminopyridine, 4-diethylaminopyridine or 4-pyrrolidinopyridine. Organic bases used in excess can also serve as solvents at the same time.

If the acids of Formula II themselves are used as acylation agents, the reaction of the amino compounds of Formula III with the carboxylic acids of Formula II can expediently also be carried out in the presence of a coupling reagent known e.g. from peptide chemistry as being suitable for amide formation. Examples of coupling reagents which promote amide formation with the free acids by reacting with the acid in situ, forming a reactive acid derivative, are in particular: ethyl chloroformate, alkylcarbodiimides, e.g. cycloalkylcarbodiimides such as dicyclohexylcarbodiimide or N-(3-dimethylaminopropyl)-N'-ethylcarbodiimide (=EDC), carbonyldiimidazole and N-lower alkyl-2-halopyridinium salts, in particular halides or toluenesulfonates. The reaction in the presence of a coupling reagent can be carried out expediently at temperatures of −30° to +50° C. in solvents such as halogenated hydrocarbons and/or aromatic solvents and optionally in the presence of an acid-binding amine described above.

In the compounds obtained by reacting the compounds of Formula II with the compounds of Formula III, wherein $R^2$ and/or $R^3$ contain free hydroxyl groups, these may if desired be reacted in known manner with a compound of Formula IV. In compounds of Formula IV, the leaving group X stands for example for halogen, preferably for chlorine.

In the compounds obtained by reacting the compounds of Formula II with the compounds of Formula III, wherein $R^2$ and/or $R^3$ contain free hydroxyl groups, these may if desired be reacted in known manner with an amino acid derivative protected by a suitable protective group. Suitable protective groups for amino acids together with methods of introducing them or selectively cleaving them are known in the art, e.g. from McOmie or from Greene. Suitably protected amino acid derivatives are either commercially available or can be prepared in a known manner.

The protective groups $R^{101}$ and $R^{401}$, provided that they do not represent any desired groups forming a biolabile ester, and/or the protective groups which may be present in any present amino acid moiety in $R^2$ and/or $R^3$, can be cleaved in known manner and if desired selectively from the compounds obtained by reacting the compounds of Formula II with the compounds of Formula III.

Compounds of Formula I may be isolated from the reaction mixture and if necessary purified in known manner, for example by high-performance liquid chromatography (=HPLC).

The starting compounds of Formula II are novel compounds which are suitable as intermediate products for the preparation of novel active substances, for example for the preparation of the compounds of Formula I. The compounds of Formula II can be prepared by reacting compounds of the general formula V,

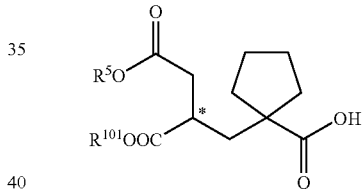

V wherein $R^5$ is an acid-protecting group and $R^{101}$ has the above meaning, with compounds of the general formula VI,

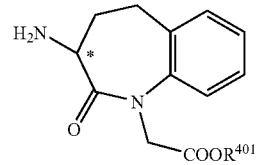

VI wherein $R^{401}$ has the above meaning, and subsequently cleaving off the acid-protecting groups $R^5$ again in known manner. The reaction can be carried out in a manner known for aminoacylations, for example corresponding to the manner indicated above for the reaction of compounds of Formula II with compounds of Formula III. To avoid undesirable secondary reactions, it may be advantageous to cleave the acid-protecting groups $R^5$ by means of a method which does not operate in alkaline medium and consequently to select correspondingly suitable acid-protecting groups $R^5$.

The amines of Formula III are known per se or can be prepared in known manner from known compounds.

The reactive acid derivatives of Formula IV are known per se or can be prepared in known manner from known compounds. These are straight-chain or branched $C_{1-4}$-carboxylic acid derivatives.

Compounds of Formula V can be prepared by reacting acrylic ester derivatives of the general formula VII,

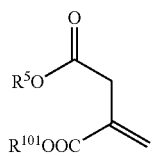

VII wherein $R^{101}$ and $R^5$ have the above meanings, with cyclopentanecarboxylic acid. The reaction can take place in known manner under the conditions of a Michael condensation in an organic solvent which is inert under the reaction conditions by reaction of the cyclopentanecarboxylic acid with a strong base capable of forming the dianion of the cyclopentanecarboxylic acid and subsequent reaction with the acrylic ester derivative of Formula VII. Suitable solvents are ethers, in particular cyclic ethers such as THF. Suitable strong bases are non-nucleophilic organic alkali metal amides or alkali metal lower alkyls such as lithium diisopropylamide or n-butyllithium. Expediently, the cyclopentanecarboxylic acid is reacted in THF with two equivalents of n-butyllithium and the reaction mixture is then reacted further with the compound of Formula VII. The reaction temperature may be between −80° and 0° C.

Compounds of Formula VI are known, for example from the specification EP 0 733 642 A1, and can be prepared in the form of their racemates or alternatively in isomerically pure form according to the methods described therein or methods analogous thereto.

Compounds of Formula VII can be prepared by esterifying compounds of the general formula VIII,

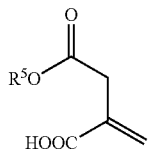

VIII wherein $R^5$ represents an acid-protecting group, in known manner with a desired alcohol.

Compounds of Formula VIII can for example obtained by reacting itaconic acid anhydride under known conditions which open the anhydride group with a reagent capable of formation of the acid-protecting group $R^5$ such as a correspondingly substituted alcohol.

In the reactions described above, the chiral centers in the starting compounds of Formula V and of Formula VI are not changed, so that depending on the type of starting compounds finally isomerically pure compounds of Formula I or isomer mixtures can be obtained. For the preparation of stereochemically uniform compounds of Formula I, expediently stereochemically uniform compounds of Formula V are reacted with stereochemically uniform compounds of Formula VI. If an enantiomerically pure compound of Formula V is reacted with a racemic compound of Formula VI or a racemic compound of Formula V with an enantiomerically pure compound of Formula VI, in each case a mixture of two diastereomers is obtained, which if desired can be separated at the stage of the compounds of Formula II or at the stage of the compounds of Formula I in known manner. The reaction of racemic compounds of Formula V with racemic compounds of Formula VI yields corresponding mixtures of four isomers, which can be separated if desired in known manner, for example by HPLC separation on possibly chiral separating materials.

The compounds of Formula V have an asymmetric or chiral center at the carbon atom bearing the radical "—$COOR^{101}$" and are obtained upon synthesis from acrylic ester derivatives of Formula VII in the form of their racemates. The optically active compounds can in principle be obtained from the racemic mixtures in a known manner, e.g. by chromatographic separation on chiral separating materials or by reaction with suitable optically active bases, e.g. α-methylbenzylamine, cinchonidine or pseudoephedrine, and subsequent separation into their optical antipodes by fractional crystallisation of the salts obtained.

The compounds of Formula I and their pharmacologically compatible salts are distinguished by advantageous pharmacological properties. In particular, the substances inhibit the enzyme NEP. NEP is an enzyme which breaks down endogenous natriuretic peptides, e.g. atrial natriuretic peptide (=ANP). Due to their inhibitory action on the NEP activity, the substances are capable of improving the biological activity and useful life of the natriuretic peptides which can be attacked by NEP, in particular ANP, and are therefore suitable for the treatment of pathological conditions which are beneficially influenced by the action of such hormones, above all of cardiovascular diseases, especially cardiac insufficiency, in particular congestive heart failure.

In congestive heart failure, a peripheral vascular resistance which is increased by reflex occurs due to a disease-induced reduced ejection fraction of the heart. This means that the myocardium has to start pumping against an increased afterload. This leads in a vicious cycle to increased strain on the heart and makes the situation even worse. The increase in the peripheral resistance is mediated, inter alia, by the vasoactive peptide endothelin (=ET-1). Endothelin is the most powerful currently-known endogenous vasoconstrictor substance and is produced from the precursor big endothelin (=Big-ET-1). According to what is currently known, various enzymes collaborate in the conversion of Big-ET-1 to ET-1, inter alia the enzymes ECE and hSEP (see on this point e.g. WO 02/094176).

In congestive heart failure, as a result of the decreased cardiac output and the increase in peripheral resistance, back-pressure phenomena of the blood occur in the pulmonary circulation and the heart itself. As a result, an increased wall tension of the heart muscle occurs in the area of the auricles and chambers. In such a situation, the heart functions as an endocrine organ and secretes, inter alia, ANP into the bloodstream. Due to its marked vasodilatory and natriuretic/diuretic activity, ANP brings about both a reduction in the peripheral resistance and a decrease in the circulating blood volume. The consequence is a marked pre- and afterload decrease. This constitutes an endogenous cardioprotective mechanism. This positive endogenous mechanism is limited in that ANP only has a very short half-life in the plasma. The reason for this is that the hormone is very rapidly broken down by NEP.

The compounds according to the invention reduce the production of endothelin by inhibiting the ECE activity and additionally inhibiting the hSEP activity and thus counteract an increase in the peripheral resistance, which consequently results in relieving myocardial strain. Results hitherto furthermore suggest that the substances according to the invention by inhibiting the NEP activity result in higher ANP levels and an extended duration of action of ANP. This should result in intensification of the ANP-mediated endogenous mechanism of cardioprotective action and impart to the substances of Formula I high effectiveness with respect to intensification of the diuretic/natriuretic ANP-induced activities.

NEP is involved not only in the breakdown of ANP but also in the breakdown of endothelin. It follows from this that pure NEP inhibition in addition to the desired increase in the ANP levels would also lead to an unfavourable increase in the endothelin levels. For this reason, a mixed profile of NEP, hSEP and a certain proportion of ECE inhibition should be regarded as particularly beneficial, since it prevents both the breakdown of the natriuretic/diuretic ANP (by NEP blockade), and simultaneously inhibits the formation of endothelin (by hSEP and ECE inhibition). As a result, a positive influence can be brought to bear on the adverse attendant effect of pure NEP inhibitors (namely undesirable increase in the endothelin levels).

The combined action profile of compounds of Formula I as inhibitors of NEP, hSEP and, to a lesser extent, also of ECE, makes the compounds according to the invention appear particularly suitable for the prophylaxis and/or treatment of pathological conditions like conditions or diseases such as cardiovascular conditions or diseases, especially cardiac insufficiency, including acute heart failure and chronic heart failure and in particular congestive heart failure; but also hypertension, including secondary forms of hypertension such as essential hypertension, renal hypertension and/or pulmonary hypertension; heart failure, angina pectoris, cardiac arrhythmias, myocardial infarction, perioperative myocardial infarction, poor prognosis myocardial infarction, cardiac hypertrophy, congestive cardiomyopathy, hypertrophic obstructive cardiomyopathy, hypertrophic non-obstructive cardiomyopathy, idiopathic cardiomyopathy, myocarditis, pericarditis and/or endocarditis in larger mammals, particularly humans. The compounds of Formula I may also be used beneficially in the prophylaxis or treatment of damage to the heart, in particular to the myocardium, induced by cardiotoxic doses of medicaments, in particular of cytostatic agents, preferably of cytostatic antibiotics or chemicals; angina abdominalis, cerebral ischaemias, peripheral vascular disease, subarachnoid haemorrhage, chronic obstructive pulmonary disease (COPD), asthma, renal disease (renal failure), atherosclerosis, and pain in cases of colorectal or prostatic carcinoma in larger mammals, particularly humans.

What is striking is the surprisingly good effectiveness of the compounds of Formula I after i.v. administration with regard to their blood pressure-regulating action, in particular their hypotensive action.

Description of the Pharmacological Test Methods

The example numbers quoted relate to the preparation examples described below.

1. In-vitro Investigation of the NEP Inhibitory Action of the Substances

To demonstrate the inhibitory action of the substances according to the invention on NEP, the inhibitory action of the substances on the hydrolytic breakdown of the polypeptide Mca-Asp-Ile-Ala-Trp-Phe-Dpa-Thr-Pro-Glu-His-Val-Val-Pro-Tyr-Gly-Leu-Gly-COOH occurring as a result of the enzymatic activity of NEP was investigated in a standard test in vitro. In this test, the measure of the inhibitory activity of the substances which was determined was their $IC_{50}$ value. The $IC_{50}$ value of a test substance having enzyme-inhibitory activity is that concentration of the test substance at which 50% of the enzymatic activity of the NEP is blocked.

Test buffer: 100 mM Tris pH 7.0, 250 mM NaCl

Enzyme: soluble, human recombinant NEP Prof. Crine, University of Montreal, Canada
  stock solution: 100 µg/ml in 20 mM Tris pH 7.0,
  Working solution: Stock solution with test buffer diluted to 2 µg/ml Substrate: Mca*-Asp-Ile-Ala-Trp-Phe-Dpa**-Thr-Pro-Glu-His-Val-Val-Pro-Tyr-Gly-Leu-Gly-COOH; a fluorescence-quenched Big-ET-1 analogue, i.e. a substrate of metalloproteases which is detectable via the fluorescence signal, in particular of NEP and ECE-1. The fluorescence of the MCA fluorophore is initially quenched by the presence of the "quencher" Dpa.

*Mca=(7-methoxycoumarin-4-yl)

**Dpa=(3-[2,4-dinitrophenyl]-L-2,3-diaminopropionyl) from Polypeptide Laboratories, Wolfenbuttel, Germany Stock solution: 100 µM in test buffer Test substances: All the substances were dissolved in DMSO (10 mM) and diluted to the concentration to be tested with test buffer.

70 µl test buffer, 10 µl enzyme working solution and 10 µl test substance solution were mixed in an Eppendorf vessel and preincubated at 37° C. for 15 minutes (=min.). Then 10 µl substrate stock solution was added and the test batch was incubated for 60 minutes at 37° C. The enzymatic reaction was then ended by 5-minutes' heating to 95° C. After centrifugation (Heraeus Biofuge B, 3 min.), the liquid supernatant was investigated by HPLC in accordance with the following specifications.

The substrate was separated from cleavage products by means of reversed-phase HPLC (CC 125/4 Nucleosil 300/5 $C_{18}$ RP column with CC 8/4 Nucleosil 100/5 C18 precolumn, from Macherey-Nagel, Duren, Germany). For this, 60 µl of the test mixture was injected into the HPLC sample injection point and the column was then eluted at a flow rate of 1 ml/min with the following gradient:

| Mobile Phase A: 100% $H_2O$ + 0.5 M $H_3PO_4$ pH 2.0 | |
|---|---|
| Mobile Phase B: 100% acetonitrile + 0.5 M $H_3PO_4$ | |
| 0–2 min. | 20% B |
| 2–6 min. | 20–60% B |
| 6–8 min. | 60% B |
| 8–10 min. | 60–90% B |
| 10–13 min. | 90% B |
| 13–15 min. | 90–20% B |

All the peptides were detected by absorption at 214 nm and by fluorescence with an excitation wavelength of 328 nm and an emission wavelength of 393 nm.

Upon enzymatic cleavage of the peptide, the fluorophore (=Mca) and the quencher end up in different peptide fragments, which reduces the effectiveness of the quench. This results in an increase in fluorescence. The increasing fluorescence signal (corresponds to the surface, A) of the HPLC peak of the peptide with the non-quenched Mca fluorophore is used for the further calculations. This signal was compared for samples with (=$A_{inhib}$) and without (=$A_{control}$) test substance of Formula I, and the value "% inhibition" was calculated on the basis of the respective peak areas according to the following formula:

% inhibition=100*(1−$A_{inhib}/A_{control}$)

All the samples were measured in duplicates and average values were calculated therefrom. A standard inhibitor (10 nM thiorphan) and a solvent control (0.1% DMSO) were likewise measured as quality controls on each run.

In this test model the test substances of Formula I listed in the following Table 1 had the $IC_{50}$ values given below:

TABLE 1

NEP-inhibiting action of the test substances in vitro

| Example No. | $IC_{50}$ (NEP) |
|---|---|
| 3 | 17.9 |
| 10 | 37 |
| 16 | 20.0 |
| 17 | <1 |
| 19 | 18.2 |
| 20 | 12.9 |
| 21 | 16.9 |
| 23 | 10.6 |
| 24 | 11.1 |
| 25 | 15.5 |
| 27 | 7.8 |
| 31 | 4.0 |
| 32 | 13.8 |
| 43 | 3.2 |
| 59 | 12 |
| 63 | 9 |
| 76 | 10.0 |

2. In Vitro Investigation of the hSEP-Inhibitory Action of the Substances

To demonstrate the inhibitory action of the substances according to the invention on hSEP, the inhibitory action of the substances on the hydrolytic breakdown of the polypeptide Mca-Asp-Ile-Ala-Trp-Phe-Dpa-Thr-Pro-Glu-His-Val-Val-Pro-Tyr-Gly-Leu-Gly-COOH occurring as a result of the enzymatic activity of the hSEP was investigated in a standard test in vitro. In this test, the measure of the inhibitory activity of the substances which was determined was their $IC_{50}$ value. The $IC_{50}$ value of a test substance having enzyme-inhibitory activity is that concentration of the test substance at which 50% of the enzymatic activity of the hSEP is blocked.

Test buffer: 100 mM Tris pH 7.0, 250 mM NaCl
Enzyme: His6-tagged hSEP ectodomain from Innogentics, Ghent, Belgium
 Stock solution: 53 mg/ml in 20 mM HEPES pH 7.2, 5% glycerol, 0.005% Tween20, 100 mM NaCl, purity >99%
 Working solution: stock solution with test buffer diluted to 10 mg/ml
Substrate: Mca-Asp-Ile-Ala-Trp-Phe-Dpa-Thr-Pro-Glu-His-Val-Val-Pro-Tyr-Gly-Leu-Gly-COOH; fluorescence-quenched Big-ET-1 analogon.
 Stock solution: 100 µM in test buffer from Polypeptide Laboratories, WolfenbUttel, Germany
Test substances: All the substances were dissolved in DMSO (10 mM) and diluted to the concentration to be tested with test buffer.

The test and the HPLC procedure were carried out analogously to the manner set forth above for determining the in vitro inhibitory action of the test substances on NEP. 10 nM phosphoramidon served as standard inhibitor in the HPLC procedure. In this test model the test substances of Formula I listed in the following Table 2 had the $IC_{50}$ values given below:

TABLE 2 hSEP-inhibiting action of the test substances in vitro

| Example No. | $IC_{50}$ (hSEP) |
|---|---|
| 2 | 21.4 |
| 3 | 7.8 |
| 10 | 25.3 |
| 16 | 15.0 |
| 17 | 24.0 |
| 19 | 9.5 |
| 20 | 36.3 |
| 23 | 17.3 |
| 24 | 27.0 |
| 25 | 3.4 |
| 27 | 26.8 |
| 28 | 11.9 |
| 31 | 12.3 |
| 43 | 2.9 |
| 56 | 2.5 |
| 59 | 4.0 |
| 76 | 4.0 |

3. In Vivo Investigation of the Inhibitory Action of the Substances on the Formation of ET-1 from Big-ET-1 in Rats To demonstrate the inhibitory action of the substances according to the invention on the formation of ET-1 from Big-ET-1, the inhibitory action of the test substances on the hydrolytic breakdown of Big-ET-1 to ET-1 occurring as a result of the enzymatic activity of ECE and related enzymes such as hSEP was investigated in a standard test in vivo. ET-1 is an endogenous strongly vasoconstrictor substance. An increase in the ET-1 level results in an increase in blood pressure. Upon infusion of Big-ET-1, an increase in blood pressure takes place to the extent that ET-1 is produced therefrom by enzyme-catalysed cleavage of Big-ET-1. As a measurement of the enzyme-inhibiting action of the substances, their inhibitory action on the increase in blood pressure induced by infusion of Big-ET-1 was determined.

Rats (Sprague-Dawley, CRLD=Charles River) were anaesthetised with 1 ml/kg Rompun/Ketavet 1:1. A pressure transducer (Statham) was inserted into the carotid artery to measure blood pressure. One jugular vein was cannulated for administering the substance, and the other for administering Big-ET-1. After a 20-minute rest phase, the rats were administered the corresponding test substance of Formula I in a concentration as a rule of 10 µmol/kg, or a vehicle. Five minutes later, 0.5 nmol/kg Big-ET-1 was infused over a period of one minute. The systolic (SAP=systolic arterial pressure) and the diastolic (DAP=diastolic arterial pressure) blood pressure and the heart rate were each measured before administration of the substance or before administration of Big-ET and in each case every five minutes over a period of 30 minutes after Big-ET administration using the pressure transducer in known manner. The maximum Big-ET-induced increase in blood pressure and the maximum lowering of heart rate were calculated from the measured values as the difference between the value measured at the moment of maximum development of the Big-ET action (typically after 5 min.) and the value measured before Big-ET infusion. Furthermore, the integral of the blood pressure curve under the influence of Big-ET-1 was determined over 30 minutes (AUC=area under the curve). The AUC value provides information about the entire extent and duration of the Big-ET action or the reduction thereof by substances; the AUC value can therefore—in addition to the maximum Big-ET action—provide additional information about the effect of the substances, for example in the event that the substances e.g. do not, or only slightly, influence the maximum Big-ET action, but considerably accelerate the subsiding of this action.

The percentage inhibition of the maximum Big-ET-1 effect on the systolic arterial blood pressure (SAP) after i.v. administration of the test substances compared with administration of a vehicle is set forth in the following Table 3:

TABLE 3

In vivo investigation of the antihypertensive properties of the test substances.

| Example No. | % substance-related inhibition of the maximum Big-ET effect on SAP vs. control | |
| --- | --- | --- |
| 2 | −53 | |
| 3 | −94 | |
| 4 | −95 | |
| 8 | −113 | |
| 14 | −59 | 3 μmol/kg |
| 16 | −45 | |
| 17 | −46 | |
| 20 | −67 | |
| 21 | −43 | |
| 23 | −40 | |
| 24 | −54 | |
| 26 | −53 | |
| 29 | −49 | |
| 32 | −52 | |
| 34 | −78 | |
| 35 | −63 | |
| 38 | −48 | 3 μmol/kg |
| 44 | −75 | |
| 59 | −98 | |
| 67 | −109 | |
| 68 | −108 | |
| 75 | −52 | 3 μmol/kg |
| 76 | −93 | |

The compound of Formula I also exhibit ECE-inhibitory properties to a certain extent. The ECE-inhibitory properties of the substances of Formula I can be demonstrated in a standard test in vitro.

The compounds of Formula I are dually acting compounds which are capable of inhibiting NEP and hSEP and are also suited for prophylaxis and/or treatment of SD.

In the clinic, SD disorders have been divided into female sexual dysfunction (FSD) disorders and male sexual dysfunction (MSD) disorders (see Melman, A. & Gingell, J. C. (1999). The epidemiology and pathophysiology of erectile dysfunction. J Urology 161: 5-11, hereinafter cited as "Melman et al. 1999"). The dually acting compounds of the invention which are capable of inhibiting NEP and hSEP, in particular the compounds of Formula I, are particularly beneficial for the prophylaxis and/or treatment of MSD (e.g. male erectile dysfunction-MED). A further advantage of the compounds of Formula I in this indication is a certain ECE inhibitory share at their profile of action.

MSD is generally associated with erectile dysfunction, also known as male erectile dysfunction (=MED) (see Benet, A. E. et al (1994), Male erectile dysfunction assessment and treatment options. C07Sp. TheY. 20: 669-673) hereinafer cited as "Benet et al. 1994"). MED is defined as: "... the inability to achieve and/or maintain a penile erection for satisfactory sexual performance (see NIH Consensus Development Panel on Impotence (1993). NIH Consensus Conference Impotence. J A. M. A. 270: 83) . . . ". It has been estimated that the prevalence of erectile dysfunction (=ED) of all degrees (minimal, moderate and complete impotence) is 52% in men 40 to 70 years old, with higher rates in those older than 70 (Melman et al. 1999). The condition has a significant negative impact on the quality of life of the patient and their partner, often resulting in increased anxiety and tension which leads to depression and low self esteem. Whereas two decades ago, MED was primarily considered to be a psychological disorder (Benet et al. 1994), it is now known that for the majority of patients there is an underlying organic cause. As a result, much progress has been made in identifying the mechanism of normal penile erection and the pathophysiology of MED.

When the dually acting compounds capable of inhibiting NEP and hSEP of the invention, in particular the compounds of Formula I, are used in the therapy of FSD, therapy of female sexual arousal disorder (=FSAD) is preferred.

FSD is best defined as the difficulty or inability of a woman to find satisfaction in sexual expression. FSD is a collective term for several diverse female sexual disorders (Leiblum, S. R. (1998). Definition and classification of female sexual disorders. Int. J. Impotence Res., 10, S104-S106; Berman, J. R., Berman, L.& Goldstein, I. (1999). Female sexual dysfunction: Incidence, pathophysiology, evaluations and treatment options. Urology, 54, 385-391.). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders. The categories of FSD are best defined by contrasting them to the phases of normal female sexual response: desire, arousal and orgasm (Leiblum, S. R. (1998). Definition and classification of female sexual disorders. Int. J. Impotence Res., 10, S104-S106).

Desire or libido is the drive for sexual expression. Its manifestations often include sexual thoughts either when in the company of an interested partner or when exposed to other erotic stimuli.

Arousal is the vascular response to sexual stimulation, an important component of which is genital engorgement and includes increased vaginal lubrication, elongation of the vagina and increased genital sensation/sensitivity.

Orgasm is the release of sexual tension that has culminated during arousal. hence, FSD occurs when a woman has an inadequate or unsatisfactory response in any of these phases, usually desire, arousal or orgasm.

FSD categories include hypoactive sexual desire disorder, sexual arousal disorder, orgasmic disorders and sexual pain disorders.

Although the compounds of the invention will improve the genital response to sexual stimulation (as in female sexual arousal disorder), in doing so they may also improve the associated pain, distress and discomfort associated with intercourse and so treat other female sexual disorders. Thus, in accordance with a particular aspect of the invention, there is provided use of a compound of the invention in the preparation of a medicament for the treatment or prophylaxis of hypoactive sexual desire disorder, sexual arousal disorder, orgasmic disorder and sexual pain disorder, more preferably for the treatment or prophylaxis of sexual arousal disorder, orgasmic disorder, and sexual pain disorder, and preferably in the treatment or prophylaxis of sexual arousal disorder. Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

FSAD is characterized by inadequate genital response to sexual stimulation. The genitalia do not undergo the engorgement that characterizes normal sexual arousal. The vaginal walls are poorly lubricated, so that intercourse is painful. Orgasms may be impeded. Arousal disorder can be caused by reduced estrogen at menopause or after childbirth and during lactation, as well as by illnesses, with vascular components such as diabetes and atherosclerosis. Other causes result from treatment with diuretics, antihistamines, antidepressants e.g. selective serotonin re-uptake inhibitors (=SSRIs) or antihypertensive agents.

Sexual pain disorders (includes dyspareunia and vaginismus) is characterized by pain resulting from penetration and may be caused by medications which reduce lubrication, endometriosis, pelvic inflammatory disease, inflammatory bowel disease or urinary tract problems. The prevalence of FSD is difficult to gauge because the term covers several types of problem, some of which are difficult to measure, and because the interest in treating FSD is relatively recent.

Many women's sexual problems are associated either directly with the female ageing process or with chronic illnesses such as diabetes and hypertension. Because FSD consists of several subtypes that express symptoms in separate phases of the sexual response cycle, there is not a single therapy.

Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (e.g. FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects. Since interest is relatively recent in treating FSD pharmacologically, therapy consists of the following: psychological counselling, over-the-counter sexual lubricants, and investigational candidates, including drugs approved for other conditions. These medications consist of hormonal agents, either testosterone or combinations of oestrogen and testosterone and more recently vascular drugs, that have proved effective in MED. None of these agents has yet been demonstrated to be effective in treating FSD.

The Diagnostic and Statistical Manual (DSM) IV of the American Psychiatric Association defines FSAD as being: "... a persistent or recurrent inability to attain or to maintain until completion of the sexual activity adequate lubrication-swelling response of sexual excitement. The disturbance must cause marked distress or interpersonal difficulty ...". The arousal response consists of vasocongestion in the pelvis, vaginal lubrication and expansion and swelling of the external genitalia. The disturbance causes marked distress and/or interpersonal difficulty. Studies investigating sexual dysfunction in couples reveals that up to 76% of women have complaints of sexual dysfunction and that 30-50% of women in the USA experience FSD (Berman, J. R., Berman, L. A., Werbin, T. J. et al. (1999). Female sexual dysfunction: Anatomy, physiology, evaluation and treatment options. Curr Opin Urology, 9,563-568). FSAD is a highly prevalent sexual disorder affecting pre-, peri- and post-menopausal (hormone replacement therapy (HRT)) women. It is associated with concomitant disorders such as depression, cardiovascular diseases, diabetes and urogenital disorders. The primary consequences of FSAD are lack of engorgement/swelling, lack of lubrication and lack of pleasurable genital sensation. The secondary consequences of FSAD are reduced sexual desire, pain during intercourse and difficulty in achieving an orgasm. It has recently been hypothesised that there is a vascular basis for at least a proportion of patients with symptoms of FSAD (Goldstein et al., Int. J. Impot. Res., 10, S84-S90, 1998) with animal data supporting this view (Park et al., Int. J. Impot. Res., 9,27-37,1997).

It is known that inhibitors of SEP enhance pelvic nerve-stimulated and vasoactive intestinal peptide (=VIP)-induced increases in vaginal and clitoral blood flow. It is also known that SEP inhibitors enhance VIP and nerve-mediated relaxations of the isolated vagina wall. Thus the present invention is advantageous as it helps provide a means for restoring a normal sexual arousal response-namely increased genital blood flow leading to vaginal, clitoral and labial engorgement. This will result in increased vaginal lubrication via plasma transudation, increased vaginal compliance and increased genital sensitivity. Hence, the present invention provides a means to restore, or potentiate, the normal sexual arousal response. By female genitalia herein it is meant: "The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands" (Gray's Anatomy, C. D. Clemente, 13th American Edition). R. J. Levin teaches that, because ". . . male and female genitalia develop embryologically from the common tissue anlagen, [that] male and female genital structures are argued to be homologues of one another. Thus the clitoris is the penile homologue and the labia homologues of the scrotal sac . . . " (Levin, R. J. (1991), Exp. Clin. Efzdocrinol., 98,6169).

With regard to MSD, in particular to MED, penile erection is a haemodynamic event which is dependent upon the balance of contraction and relaxation of the corpus cavernosal smooth muscle and vasculature of the penis (see Lerner, S. E. et al (1993). A review of erectile dysfunction: new insights and more questions. J. Urology 149: 1246-1255). Corpus cavernosal smooth muscle is also referred to herein as corporal smooth muscle or in the plural sense corpus cavernosa. Relaxation of the corpus cavernosal smooth muscle leads to an increased blood flow into the trabecular spaces of the corpus cavernosa, causing them to expand against the surrounding tunica and compress the draining veins. This produces a vast elevation in cavernosal blood pressure which results in an erection (see Naylor, A. M. (1998). Endogenous neurotransmitters mediating penile erection. Br. J. Urology 81: 424-431), hereinafter cited as "Naylor, 1998"). The changes that occur during the erectile process are complex and require a high degree of coordinated control involving the peripheral and central nervous systems, and the endocrine system (Naylor, 1998). Corporal smooth muscle contraction is modulated by sympathetic noradrenergic innervation via activation of postsynaptic α-adrenoceptors. MED may be associated with an increase in the endogenous smooth muscle tone of the corpus cavernosum. However, the process of corporal smooth muscle relaxation is mediated partly by non-adrenergic, non-cholinergic (=NANC) neurotransmission. There are a number of other NANC neurotransmitters found in the penis, other than nitric oxide (=NO), such as calcitonin gene related peptide (=CGRP) and VIP. The main relaxing factor responsible for mediating this relaxation is NO, which is synthesised from L-arginine by nitric oxide synthase (=NOS) (see e.g. Taub, H. C. et al (1993). Relationship between contraction and relaxation in human and rabbit corpus cavernosum. Urology 42: 698-704). It is thought that reducing corporal smooth muscle tone may aid NO to induce relaxation of the corpus cavernosum. During sexual arousal in the male, NO is released from neurones and the endothelium and binds to and activates soluble guanylate cyclase (sGC) located in the smooth muscle cells and endothelium, leading to an elevation in intracellular cyclic guanosine 3',5'-monophosphate (cGMP) levels. This rise in cGMP leads to a relaxation of the corpus cavernosum due to a reduction in the intracellular calcium concentration ([Ca2+] i), via unknown mechanisms thought to involve protein kinase G activation (possibly due to activation of $Ca^{2+}$ pumps and $Ca^{2+}$-activated $K^+$-channels).

Recently it has been shown that c-type natriuretic peptide (=CNP) may also play a role in MED, acting at the membrane-bound guanylyl cyclase B (=GC-B) which is expressed in human corpus cavernosum tissue. Stimulation of GC-B leads to an increase in intracellular cGMP and, consequently, smooth muscle relaxation. PDE5-inhibitors, e.g. sildenafil increase intracellular cGMP in corpus cavernosum tissue by inhibiting its breakdown. PDE5-inhibitors are inactive in the absence of a stimulator of cGMP formation, e.g. in the absence of NO. This finding suggests that the basal (unstimulated) rate of cGMP formation in the corpus cavernosum is rather low, so that inhibition of cGMP breakdown by PDE5 inhibitors is not sufficient for an erectile response without concomittant stimulation of guanylyl cyclase. Increasing the concentration of CNP leads to elevated intracellular cGMP concentration, by an increase in cGMP formation. Consequently, elevating the CNP concentration in the corpus cavernosum will presumably have similar effects as inhibiting PDE5. Due to their different mechanisms of action, i.e. increasing formation of cGMP vs. inhibition of its breakdown, the approaches of inhibiting PDE5 or the breakdown of CNP, respectively are deemed to be additive thus making it a reasonable assumption that a combination of these two mechanisms of action will be particularly effective in patients who do not respond to the administration of PDE5 inhibitors alone.

VIP positive nerve fibres have been found in the trabecular meshwork of the corpus cavernosum, suggesting a role of VIP release in penile erection. Effects of VIP are thought to be mediated via increases in cAMP and are thus complementary to those of cGMP-elevating agents. In patients with ED an intracavernosal injection of VIP (combined with the α-adrenoceptor antagonist phentolamine) was found to be a safe and effective treatment, with a response rate of 67% (erections sufficient for sexual intercourse).

The endopeptidases NEP and hSEP both degrade CNP and VIP and thereby limit the effects of CNP and VIP on cavernosal smooth muscle. Inhibition of CNP and VIP breakdown will lead to increased availability of these vasorelaxing factors thereby increasing blood flow to the corpus cavernosum which finally should result in improved erectile function. Support can be found for this from experimental data in rabbits, showing a significant increase in intracavernosal pressure and female genital blood flow after application of an NEP-inhibitor (see document WO 02/079143). Furthermore, a gene (SMR1) encoding a propeptide of the endogenous NEP-inhibitor sialorphine was found (see User H. M., Zelner D. J., McKenna K. E., McVary K. T. (2003). Microarray analysis and description of SMR1 gene in rat penis in a post-radical prostatectomy model of erectile dysfunction. J Urol.; 170(1):298-301) to be markedly downregulated (>80-fold) in a rat model of neurogenic erectile dysfunction suggesting that in this disease NEP activity may be enhanced and contribute to the development of erectile dysfunction.

Description of the Pharmacological Test Method

The example numbers quoted relate to the preparation examples described below. The inhibition of the enzymatic breakdown of CNP and VIP by the compounds used according to the invention was measured in an enzymatic in vitro assay according to the following protocol:

Enzymes: a) hSEP (sol hu)(his)$_6$; or: His6-tagged hSEP ectodomain. stock solution: 53 µg/ml in 20 mM HEPES pH 7.2, 5% glycerol, 0.005% Tween20, 100 mM NaCl, purity >99% working solution: stock solution diluted with assay buffer to 5 µg/ml Supplier: Innogenetics, Ghent, Belgium. Preparation and purification of the protein were performed as described in WO 02/094176.

b) NEP (prepared from pig kidney cortex)

stock solution: 120 µg/ml in 20 mM bisTris, purity >95% working solution: stock solution diluted with assay buffer to 5 µg/ml

Supplier: Dr. Philippe Crine, Univ. of Montreal, Canada

Substrates: a) VIP b) CNP (32-53)

stock solution: 100 µM in assay buffer

Supplier: Bachem, Weil am Rhein, Germany

Assay buffer: 100 mM Tris pH 7.0, 250 mM NaCl

All test compounds were dissolved in DMSO at 10 mM and further diluted with assay buffer.

Activity Assay Procedure

80 µl of assay buffer, 10 µl of enzyme working solution (NEP or hSEP) and 10 µl of peptide stock solution (VIP or CNP) were mixed in an Eppendorf vial and incubated for 120 min. at 37° C. The enzymatic reaction was subsequently terminated by heating to 95° C. for 5 min. After centrifugation (Heraeus Biofuge B, 3 min) the supernatant was subjected to HPLC.

Inhibition Assay Procedure

70 µl of assay buffer, 10 µl of enzyme working solution (NEP or hSEP) and 10 µl of a test compound solution were mixed in an Eppendorf vial and preincubated at 37° C. for 15 minutes. Then, 10 µl of peptide stock solution (VIP or CNP) was added and the reaction mixture was incubated at 37° C. for 60 min. to allow enzymatic hydrolysis. The enzymatic reaction was subsequently terminated by heating to 95° C. for 5 min. After centrifugation (Heraeus Biofuge B, 3 min) the supernatant was subjected to HPLC. In order to separate the remaining substrate from the cleavage products, a reversed phase HPLC technique with a CC 125/4 Nucleosil 300/5 $C_{18}$ RP column and a CC 8/4 Nucleosil 100/5 C18 precolumn (Macherey-Nagel, Düren, Germany) was used. 60 µl of the reaction samples were injected into the HPLC and the column was eluted at a flow rate of 1 ml/min with the following gradient:

Solution A: 100% H2O + 0.5 M H3PO4 pH 2.0
Solution B: 100% acetonitrile + 0.5 M H3PO4

| | |
|---|---|
| 0–2 min: | 5% B |
| 2–7 min: | 5–50% B |
| 7–8 min: | 50–90% B |
| 8–10 min: | 90% B |
| 10–12 min: | 90–5% B |

All peptides were detected by absorbance at 214 nm (UV spectroscopy).

The percentage (=%) of hydrolysis was calculated on the basis of the peak area of the undegraded peptide for an enzyme containing sample Y in correlation to a sample containing the same concentration of peptide without enzyme (blank) by the following equation:

% hydrolysis=100*(blank−Y)

Basis of the calculation of % inhibition is the peak area of the undegraded peptide (VIP or CNP) for an inhibitor containing sample X in comparison to samples containing only peptide (blank) or peptide and enzyme without inhibitor (control) according to the following equation:

% inhib=100*(X−control)/(blank−control)

All samples were run in duplicate and mean values were used. A solvent control (0.1% DMSO) was added to each assay run. CNP and VIP were cleaved by NEP and hSEP in vitro. Breakdown of both peptides was faster with hSEP than with NEP, as is shown in the following Table 4.

TABLE 4

Breakdown rates of VIP and CNP by NEP or hSEP

| | breakdown of CNP | | breakdown of VIP | |
|---|---|---|---|---|
| | hSEP | NEP | hSEP | NEP |
| degradation at t = 2 h | 46% | 39% | 36% | 28% |

The test compounds according to the invention were able to prevent degradation of CNP and VIP by both NEP and SEP. In this test model the test substances of Formula I listed in Table 5 below had the $IC_{50}$ values given below:

TABLE 5

Prevention of degradation of CNP and VIP by the test compounds

| inhibition of | breakdown of CNP | | breakdown of VIP | |
|---|---|---|---|---|
| breakdown by example no. | hSEP $IC_{50}$ (nM) | NEP $IC_{50}$ (nM) | hSEP $IC_{50}$ (nM) | NEP $IC_{50}$ (nM) |
| 4 | 1.0 | 10.1 | 3.1 | 3.1 |

The compounds of Formula I are also suited for the prophylaxis and/or treatment of adverse conditions associated with apoptosis. Examples of adverse conditions associated with apoptosis include:

neuro-degenerative disorders such as e.g. ischemic stroke, cerebral ischemia, traumatic brain injury, acute disseminated encephalomyelitis, amyotrophic lateral sclerosis (ALS), retinitis pigmentosa, mild cognitive impairment, Alzheimer's disease, Pick's disease, senile dementia, progressive supranuclear palsy, subcortical dementias, Wilson disease, multiple infarct disease, arteriosclerotic dementia, AIDS associated dementia, cerebellar degeneration, spinocerebellar degeneration syndromes, Friedreichs ataxia, ataxia telangiectasia, epilepsy related brain damage, spinal cord injury, restless legs syndrome, Huntington's disease and Parkinson's disease, striatonigral degeneration, cerebral vasculitis, mitochondrial encephalo-myopathies, neuronal ceroid lipofuscinosis, spinal muscular atrophies, lysosomal storage disorders with central nervous system involvement, leukodystrophies, urea cycle defect disorders, hepatic encephalopathies, renal encephalopathies, metabolic encephalopathies, porphyria, bacterial or viral meningitis and meningoencephalitis, prion diseases, poisonings with neurotoxic compounds, Guillain Barre syndrome, chronic inflammatory neuropathies, polymyositis, dermatomyositis, radiation-induced brain damage; gastrointestinal disorders like irritable bowel disease and inflammatory bowel diseases, Crohn's disease and ulcerative colitis, coeliac disease, *Helicobacter pylori* gastritis and other infectious gastritides, necrotizing enterocolitis, pseudomembranous enterocolitis, radiation-induced enterocolitis, lymphocytic gastritis, graft-versus-host disease, acute and chronic pancreatitis;

hepatic diseases such as e.g. alcoholic hepatitis, viral hepatitis, metabolic hepatitis, autoimmune hepatitis, radiation-induced hepatitis, liver cirrhosis, hemolytic uremic syndrome, glomerulonephritis, lupus nephritis, viral diseases such as fulminant hepatitis;

joint-diseases such as trauma and osteoarthritis;

immuno-suppression or immunodeficiency, in particular autoimmune diseases like idiopathic inflammatory myopathy, chronic neutropenia, thrombotic thrombocytopenic purpura, rheumatoid arthritis, idiopathic thrombocytopenic purpura, autoimmune haemolytic syndromes, antiphospholipid antibody syndromes, myocarditis, multiple sclerosis and its diagnostic sub-classifications relapsing-remitting multiple sclerosis, secondary progressive multiple sclerosis, primary progressive multiple sclerosis, progressive relapsing multiple sclerosis, acute multiple sclerosis, benign relapsing multiple sclerosis or asymptomatic multiple sclerosis, neuromyelitis optica (Devic's syndrome), lymphocytic hypophysitis, Grave's disease, Addison's disease, hypoparathyroidism, type 1 diabetes, systemic lupus erythematodes, pemphigus vulgaris, bullous pemphigoid, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome and fibromyalgia;

myelodysplasias such as aplastic anemia;

dermatological diseases including pemphigous vulgaris, dermatomyositis, atopic dermatitis, Henoch-Schonlein purpura, acne, systemic sclerosis, seborrhoeic keratosis, cutaneous mastocytosis, chronic proliferative dermatitis, dyskeratosis, scleroderma, interstitial granulomatous dermatitis, psoriasis, bacterial infections of the skin, dermatomycoses, lepra, cutaneous leishmaniasis, vitiligo, toxic epidermal necrolysis, Steven Johnson syndrome, sebaceous adenoma, alopecia, photodamage of the skin, lichen sclerosus, acute cutaneous wounds, incontinentia pigmenti, thermal damage of the skin, exanthematous pustulosis, lichenoid dermatosis, cutaneous allergic vasculitis, cytotoxic dermatitis;

diseases of the inner ear such as e.g. acoustic trauma-induced auditory hair cell death and hearing loss, aminoglycoside induced auditory hair cell death and hearing loss, ototoxic drug-induced hearing loss, perilymphatic fistula, cholesteatoma, cochlear or vestibular ischemia, Meniere's disease, radiation-induced hearing loss, hearing loss induced by bacterial or viral infections and idiopathic hearing loss;

transplantation: graft-versus-host disease, acute and chronic rejection of heart-, lung-, kidney-, skin-, corneal-, bone marrow- or liver-transplants;

wound healing and tissue rejection.

The usefulness of the amidomethyl-substituted 1-(carboxyalkyl)-cyclopentylcarbonylamino-benzazepine-N-acetic acid derivatives of Formula I for the prophylaxis and treatment of said adverse conditions associated with apoptosis can be demonstrated in suitable animal models predictive of anti-apoptotic activity.

Description of the Pharmacological Test Methods

The example numbers quoted relate to the preparation examples described below.

1. Traumatic Brain Injury: Delayed Apoptotic Neuronal Death

Contusing device. The contusing device consisted of a stainless steel tube, 40 cm in length, perforated at 1 cm intervals to prevent air compression in the tube. Adult Wistar rats, 230-270 g, were anesthetized with chloral hydrate, 400 mg/kg i.p., a craniotomy over the right hemisphere was made, the device guiding a falling weight onto the footplate resting upon the surface of the dura was placed perpendicular to the surface of the skull, and a force of 380 g×cm produced by a 20 g weight was selected to produce brain contusion. A maximum of 2.5 mm depression of the brain surface was allowed to avoid mechanical puncture of the dura. The center of the footplate was stereotaxically positioned 1.5 mm posterior and 2.5 mm lateral to the bregma. The rats underwent perfusion fixation 3 days after brain injury with a solution containing 4% paraformaldehyde in phosphate buffer.

Intracerebroventricular injections: Compounds were administered intracerebro-ventricularly (=i.c.v.) by means of a Hamilton syringe in a volume of 5-15 µl. Injections were performed over 5 min, 15 min-8 hrs after trauma using the following stereotaxic coordinates: AP=−0.5 mm, L=−2 mm and V=−5.5 in relation to bregma (Swanson, L. W. (1992) Brain Maps: Structure of the Rat Brain, Elsevier, Amsterdam).

Morphometric analysis in hippocampus. The damage in the hippocampal CA3 subfield was determined stereologically at 5 different rostrocaudal levels extending from 10.21 to 11.21 mm (Swanson, L. W. (1992) Brain Maps: Structure of the Rat Brain, Elsevier, Amsterdam) and throughout its mediolateral axis three days after traumatic injury. To quantitatively assess neuronal loss in the hippocampus, stereological disector technique (Cruz-Orive, L. M. & Weibel, E. R. (1990) Am. J. Physiol. 258, L148-L156) was used to estimate numerical density (Nv) of pyramidal neurons. An unbiased counting frame (0.05 mm×0.05 mm; disector height 0.01 mm) and a high-aperture objective (×40) were used for sampling. Normal neurons were identified by the presence of the typical nuclei with clear nucleoplasm and distinct nucleolus surrounded by cytoplasm containing Nissl substance. The border between CA2 and CA3 subfields was considered as the point where the looser arrangement of large pyramidal cells goes into densely packed pyramidal cells of the subfield CA3. An arbitrary line connecting the lateral ends of the dentate granule cell layers was considered a junction between subfields CA3 and CA4.

In this test model the test substance of Example 3 elicited a dose-dependent neuroprotective effect. A neuroprotective effect was still evident when the test substance of Example 3 was administered i.c.v. up to 8 hrs after trauma:

Dose response of the neuroprotective effect of the test substance of Example 3 when administered i.c.v. 15 min after trauma to adult Wistar rats was measured. Neuronal densities were determined in the CA3 hippocampal subfield as described in the methods. Densities of CA3 neurons ± Standard Error of Measurement (=SEM) in 6 stereotactic levels in the left non-traumatized side of vehicle treated rats and the traumatized right side of vehicle treated rats and in rats treated with the test substance of Example 3 were measured and the results listed in table 6 below.

In all of the following tables the numbers ("n") indicate the number of rats per group, where applicable.

TABLE 6

| Neuronal densities CA3 hippocampus, cells × $10^3/mm^3$ | | | | | |
|---|---|---|---|---|---|
| Stereotactic level | Vehicle left; (n = 10) | Vehicle right; (n = 10) | Compound of Ex. 3, 3 µg; (n = 10) | Compound of Ex. 3, 10 µg; (n = 10) | Compound of Ex. 3, 30 µg; (n = 10) |
| 10.21 | 159.00 ± 3.62 | 91.20 ± 7.60 | 98.40 ± 4.39 | 108.60 ± 4.30 | 108.40 ± 3.15 |
| 10.41 | 158.20 ± 3.03 | 87.20 ± 8.17 | 89.00 ± 5.05 | 108.60 ± 5.34 | 105.20 ± 5.76 |
| 10.61 | 157.20 ± 2.88 | 66.80 ± 7.68 | 72.80 ± 6.01 | 111.40 ± 7.09 | 94.20 ± 5.10 |
| 10.81 | 159.60 ± 2.99 | 56.80 ± 5.96 | 84.20 ± 6.47 | 112.00 ± 6.42 | 83.20 ± 7.10 |
| 11.01 | 152.40 ± 2.99 | 51.40 ± 6.89 | 86.00 ± 7.44 | 111.40 ± 7.11 | 80.20 ± 7.45 |
| 11.21 | 151.60 ± 2.47 | 71.60 ± 8.22 | 95.40 ± 6.96 | 119.20 ± 3.70 | 90.00 ± 9.24 |

Injection of vehicle resulted in the decrease of neuronal densities in the CA3 hippocampus up to 35% of control values, while injection of 3, 10 or 30 µg of the test substance of Example 3 partially prevented hippocampal neuronal loss, with the dose of 10 µg being most effective. Analysis of variance ("ANOVA") revealed that there was a significant protective effect of treatment on neuronal loss in the CA3 hippocampus for all three tested doses of the test substance of Example 3 (P<0.001; n=10 per group). ANOVA also revealed that the dose of 10 µg conferred significantly better neuroprotection than the doses of 3 µg or 30 µg.

The time window of the neuroprotective effect of test substance of Example 3 when administered i.c.v. 2, 4 or 8 hrs after trauma to adult Wistar rats was measured. Neuronal densities were determined in the CA3 hippocampal subfield as described in the methods. Densities of CA3 neurons ±SEM in 6 stereotactic levels in the traumatized right side of rats treated with either vehicle or the test compound of Example 3 were measured and the results listed in table 7 below.

TABLE 7

Neuronal densities CA3 hippocampus, cells × 10³/mm³

| Stereo-tactic level | Vehicle right; (n = 8) | Compound of Ex. 3, 2 hrs; (n = 8) | Compound of Ex. 3, 4 hrs; (n = 8) | Compound of Ex. 3, 8 hrs; (n = 8) |
|---|---|---|---|---|
| 10.21 | 55.21 ± 5.81 | 72.30 ± 4.80 | 72.20 ± 5.70 | 62.00 ± 4.90 |
| 10.41 | 50.65 ± 7.30 | 68.10 ± 6.30 | 65.90 ± 8.80 | 53.00 ± 6.44 |
| 10.61 | 49.35 ± 8.76 | 60.80 ± 5.60 | 63.00 ± 6.30 | 53.00 ± 6.00 |
| 10.81 | 51.21 ± 7.97 | 60.20 ± 9.40 | 60.50 ± 10.50 | 52.50 ± 4.48 |
| 11.01 | 54.80 ± 10.30 | 63.00 ± 11.70 | 62.20 ± 13.50 | 61.80 ± 4.48 |
| 11.21 | 60.00 ± 13.00 | 67.70 ± 14.00 | 66.30 ± 15.90 | 65.90 ± 4.90 |

Injection of vehicle resulted in decrease of neuronal densities in the CA3 hippocampus up to 35% of control values. Intracerebroventricular injection of 10 μg of the test substance of Example 3 partially prevented hippocampal neuronal loss. ANOVA revealed that there was a significant effect of treatment with of the test substance of Example 3 on neuronal loss in the CA3 hippocampus for all three time points (P<0.001 at 2 and 4 hrs, P<0.01 for 8 hrs).

2. Adriamycin Toxicity: Determination of Anti-apoptotic Activity

Wistar rats, weighing 200-250 g, were anesthetized with chloral hydrate, 400 mg/kg, and Alzet osmotic minipumps (2ML1), were implanted subcutaneously (=s.c.). The pumps had been filled with either vehicle or solution containing compounds of the invention at the appropriate concentration and primed prior to implantation. Animals subsequently received adriamycin at three equal daily doses of 5 mg/kg i.p. on days 1, 2 and 3. Rats were euthanized 5 days after the first injection of adriamycin and transcardially perfused with a solution containing 4% paraformaldehyde in phosphate buffer. The heart, liver and kidneys were subsequently removed and embedded in parafin.

TUNEL staining: For terminal deoxynucleotide transferase-mediated dUTP nick end-label (TUNEL) based histological analysis, organs were post-fixed for 5 days at 4° C. and paraffin-embedded. TUNEL staining was performed on 10 μm thick paraffin sections using the ApopTag Peroxidase kit (S 7100, Oncor Appligene, Heidelberg, Germany) according to the manufacturer's instructions. Briefly, after pretreatment with proteinase K and quenching of endogenous peroxidase, sections were incubated in equilibration buffer followed by working strength TdT enzyme (incorporating digoxigenin labeled dUTP nucleotides to free 3'-OH DNA termini), (1 hr, 37° C.). Sections were incubated in stop/wash buffer (30 min, 37° C.), then with anti-digoxigenin-peroxidase conjugate (30 min) followed by DAB substrate (Sigma, Deisenhofen, Germany) and lightly counterstained with methylgreen.

In this test model the test substance of Example 4 conferred significant protection against adriamycin toxicity in the heart, liver and kidney in that it significantly reduced the densities of TUNEL positive cells in the three organs. This effect was dose-dependent with the dose of 100 mg/kg and day being the most effective:

Wistar rats were administered adriamycin at the cumulative dose of 15 mg/kg i.p. The test substance of Example 4 was administered s.c. at the doses of 20, 50 or 100 mg/kg and day by means of Alzet osmotic minipumps over 5 days. Animals were euthanized and transcardially perfused 5 days after the first injection of adriamycin and the heart, kidney and liver were processed for TUNEL staining. Densities of TUNEL positive cells were determined as described in the methods. Results for each organ (heart, liver, kidney) were measured as mean densities of TUNEL positive cells ±SEM for the control groups and the different test groups (20, 50 or 100 mg/kg and day of test compound of Example 4) and listed in table 8 below.

TABLE 8

TUNEL positive cells/mm³ × 10²

| | Heart | Liver | Kidney |
|---|---|---|---|
| Adriamycin (n = 24) | 5.417 ± 0.146 | 10.420 ± 0.275 | 9.438 ± 0.198 |
| + Compound of Ex. 4; 20 mg/kg (n = 10) | 4.350 ± 0.248*** | 8.750 ± 0.301** | 7.900 ± 0.306*** |
| + Compound of Ex. 4; 50 mg/kg (n = 10) | 3.700 ± 0.260*** | 8.250 ± 0.271*** | 7.850 ± 0.587** |
| + Compound of Ex. 4; 100 mg/kg (n = 10) | 3.550 ± 0.157*** | 7.450 ± 0.329*** | 6.300 ± 0.260*** |

The test substance of Example 4 dose-dependently decreased the cytotoxic effect of adriamycin in all three organs. Comparisons between groups were performed by means of Student's t test (P<0.01; *P<0.001 compared to vehicle treated rats).

The present invention also provides a method of treating or preventing cardiovascular disorders or diseases and/or treatment of adverse conditions associated with apoptosis in mammals and humans comprising administering to a subject in need thereof an effective amount of a compound of Formula I.

The present invention further provides a method of treating or preventing sexual dysfunction in mammals and humans comprising administering to a subject in need thereof an effective amount of a dually acting compound capable of inhibiting NEP and hSEP, in particular of a compound of Formula I, according to the invention.

The compounds of Formula I may be administered in conventional pharmaceutical compositions. The doses to be used may vary individually and will naturally vary according to the type of condition to be treated and the substance used. In general, however, medicinal forms with an active substance content of 0.2 to 500 mg, in particular 10 to 200 mg, active substance per individual dose are suitable for administration to humans and larger mammals. The agents of the present invention may also be administered by intravenous infusion, at a dose which is likely to range from 0.001-10 mg/kg/hr. The above dosages are exemplary of the average case. The compounds may be contained according to the invention, together with conventional pharmaceutical auxiliaries and/or excipients, in solid or liquid pharmaceutical compositions. Examples of solid pharmaceutical compositions are compositions which can be administered orally, such as tablets, coated tablets, capsules, powders or granules, or alternatively suppositories. These pharmaceutical compositions may contain conventional pharmaceutical inorganic and/or organic excipients, such as talcum, lactose or starch, in addition to conventional pharmaceutical auxiliaries, for example lubricants or tablet disintegrating agents. Liquid pharmaceutical compositions such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or excipients in known manner. For the preparation of solid medicament forms, the active substances may for example be mixed with the auxiliaries and/or excipients in conventional manner and may be wet or dry granulated. The granules or powder may be poured directly into capsules or be pressed into tablet cores in conventional manner. These may be coated in known manner if desired.

The following examples are intended to explain the invention further, without limiting its scope.

The mass spectra were measured using the following method:

HPLC-MS: API100 Quadrupol mass spectrometer (PE Applied Biosystems) coupled to a LC200 pump (PE). Electrospray ionisation, positive mode. Scan range m/z 100 to 1000. Software MassChrom 1.2. Xterra® column (4.6 mm×50 mm, 2.5 μm).

Solvent system: Water (10 mM ammonium acetate, pH 5) and acetonitrile, linear gradient from 5% acetonitrile to 95% in 10 min.

EXAMPLE 1

Ethyl 2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}-4-(isopropylamino)-4-oxobutyrate

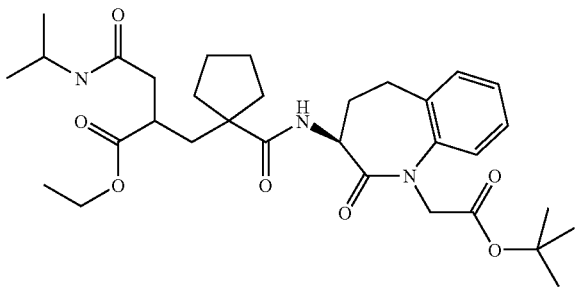

A) 91.9 ml benzyl alcohol was added to 99.07 g itaconic acid anhydride and the mixture was stirred for 8 hours (=h) at 65° C. The crystals produced on cooling were made into a slurry with 35 ml of a mixture of n-hexane/diethyl ether 2:1 (v/v) and filtered off from the solvent. The resulting crude product was dissolved in 150 ml diethyl ether in warm conditions and crystallised again by addition of 80 ml n-hexane. The combined mother lyes were reduced, recrystallised corresponding to the above method and the crystals obtained were finally added to the main quantity. 120 g 2-[(2-benzyloxy)-2-oxoethyl]acrylic acid was obtained which was used directly for the next reaction without further purification, $^1$H-NMR (CDCl$_3$): 7.35, m, [5]; 6.47, s, [1]; 5.83, s, [1]; 5.15, s, [2]; 3.40, s, [2] ppm.

B) 100 g of the 2-[(2-benzyloxy)-2-oxoethyl]acrylic acid obtained above was suspended in 100 ml methyl-tert. butylether (=MTBE) and 0.5 ml pyridine was added thereto. 47 ml thionyl chloride was added dropwise thereto and the resulting mixture was heated for 1.5 hours under reflux cooling to boiling. After cooling to room temperature, it was evaporated approximately to dryness at reduced pressure. The resulting residue was dissolved in 50 ml dichloromethane and added dropwise at 0-5° C. to a receiving solution consisting of 16 ml ethanol and 36.5 ml triethylamine in 150 ml dichloromethane. Once addition had ended, stirring was continued for 1 hour at approx. 0° C. Then it was washed in succession twice with 250 ml water each time, once with 100 ml dilute aqueous sodium bicarbonate solution and finally once with saturated aqueous common salt solution. The organic phase was dried over sodium sulfate and evaporated as far as possible under reduced pressure. Distillation of the resulting residue at 0.015 mbar and 150° C. yielded 56.3 g 2-methylenesuccinic acid-4-benzylester-1-ethylester, which was used without further purification or characterisation directly for the next reaction.

C) 118 ml diisopropylamine was dissolved in 3 l dry tetrahydrofuran (=THF) under nitrogen atmosphere and the solution was cooled to 0° C. 340 ml of a 2.5 M solution of n-butyllithium in n-hexane was added to this receiving solution and stirring was continued for another 45 minutes at 0° C. once the addition had ended. Then a solution of 45 g cyclopentanecarboxylic acid in 100 ml dry THF was dropped into the resulting mixture at 0-5° C. and the mixture was then stirred for 2 hours at 0° C. It was cooled to −80° C. and a solution of 72.6 g of a 2-methylenesuccinic acid-4-benzylester-1-ethylester as obtained above (total quantity from several batches) in 100 ml THF was added dropwise thereto. It was stirred for 2 hours at −75° C. and then 1.5 l of a 2N aqueous hydrochloric acid was added. After thawing and phase separation, the aqueous phase was extracted twice with ethyl acetate (=EA), the organic phases were combined and dried over sodium sulfate. The solvent was evaporated at reduced pressure and volatile substances were separated off by distillation at 0.02 mbar and 140° C. Chromatography of the residue remaining after distillation on silica gel (mobile phase: EA/n-hexane 1:6 to 1:7 v/v) yielded 22.8 g 1-[4-(benzyloxy)-2-(ethoxycarbonyl)-4-oxobutyl]cyclopentanecarboxylic acid; $^1$H-NMR (CDCl$_3$): 7.33, m, [5]; 5.10, s, [2]; 4.04, m, [2]; 2.88, m, [1]; 2.80-2.48, AB-Q., [2]; 2.2-2.1, m, [2]; 1.7-1.4, m, [6]; 1.20, tr, [3].

D) 49.5 g of a 1-[4-(benzyloxy)-2-(ethoxycarbonyl)-4-oxobutyl]cyclopentanecarboxylic acid as obtained above (total quantity from several batches) was dissolved in 435 ml dichloromethane. 39.5 g tert. butyl-[(3S)-3-amino-2-oxo-2,3,4,5-tetrahydro-1H-1-benzazepin-1-yl]acetate (for production see EP 0 733 642 A1), 18.3 g hydroxybenzotriazole and 60 ml morpholine were added to this receiving solution. Then 52 g EDC×HCl was added to the resulting mixture in one portion and stirring was carried out overnight at room temperature. Then the solvent was evaporated at reduced pressure and the remaining residue was taken up in 750 ml of EA. The organic phase was washed in succession twice with 100 ml 2N aqueous hydrochloric acid each time, twice with 100 ml water each time and once with 100 ml saturated aqueous common salt solution and dried over sodium sulfate. Evaporation of the solvent at reduced pressure and drying of the remaining residue in an oil pump vacuum (5×10$^{-2}$ mbar) yielded 87.9 g 2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}succinic acid-4-benzylester-1-ethylester as yellowish oil, which was used without further purification or characterisation for the subsequent reaction.

E) 87.9 g of the 2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}succinic acid-4-benzylester-1-ethylester obtained above was dissolved in 600 ml ethylacetate (=EA) and 20 g palladium on activated carbon (=Pd/C) was added thereto. It was hydrogenated for 2 hours at a hydrogen pressure of 1 bar and the reaction mixture was then filtered over Cellite. The filter cake was subsequently washed with 1.5 l EA and the combined organic phases were very largely evaporated at reduced pressure. The residue was taken up in 500 ml EA/cyclohexane (1:1, v/v) and extracted twice with 200 ml semi-saturated Na$_2$CO$_3$ solution each time. The aqueous phase was acidulated with conc. KHSO$_4$ solution and extracted 3 times with 200 ml EA each time. After drying over sodium sulfate, it was evaporated under reduced pressure. Drying of the remaining residue in an oil pump vacuum yielded 71 g 3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-ethoxy-4-oxobutyric acid as white foam, $^1$H-NMR (CDCl$_3$): 7.31-7.17, m, [3]; 7.11, d, [0.5]; 7.08, d, [0.5]; 6.81, d, [0.5]; 6.73, d, [0.5].

The intermediate product obtained in this case can if desired be separated into its diastereomerically pure constituents by preparative high-performance liquid chromatography (=HPLC). 70 g of the intermediate product obtained above was separated off using the method set forth below:

Column: LC80-1, 23.4×8 cm; stationary phase: 740 g ChiralpakAD, 20 p; mobile phase: heptane/isopropanol (85:15); UV detection; cycle time: 45 minutes;

Analysis: stationary phase: Chiralpak AD, 20 p; mobile phase: heptane/isopropanol 9:1 (v/v), flow rate: 2 ml/min; cycle time: 15 minutes.

With a retention time of 11.6 min., there was obtained 30 g of the first stereoisomer, which was assigned the designation "rel1" in relation to the chiral center "*C$_a$" bearing the group —COOR$^1$, as (2"rel1")-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-ethoxy-4-oxobutyric acid, $^1$H-NMR (CDCl$_3$): 7.31-7.18, m, [3]; 7.09, d, [1]; 6.74, d, [1]; 4.53, 4.48, 4.37, 4.32, AB-Q., [2]; 4.48, m, [1]; 4.11, m, [1].

With a retention time of 6.5 min., there was obtained 33 g of the second stereoisomer, which was assigned the designation "rel2" in relation to the chiral center "*C$_a$" bearing the group "—COOR$^1$", as (2"rel2")-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]ethyl}4-ethoxy-4-oxobutyric acid, $^1$H-NMR (CDCl$_3$): 7.31-7.17, m, [3]; 7.11, d, [2]; 6.81, d, [1]; 4.60, 4.56, 4.35, 4.31, AB-Q. [2]; 4.48, m, [1]; 4.10, m, [1]; [α]$_D$=−136° (1% in methanol).

F) 4 g of the 3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-ethoxy-4-oxobutyric acid obtained above was dissolved in 15 ml dichloromethane. After this receiving solution had been cooled to 0° C., 1.12 ml triethylamine and 0.77 ml ethyl chloroformate were added slowly dropwise thereto in succession and the mixture was stirred for 30 minutes at 0° C. Then 0.94 ml of isopropylamine was added thereto and stirring was continued for a further 3 hours at 0° C. The solvent was largely evaporated at reduced pressure and the remaining residue was taken up in 100 ml EA. The organic phase was washed in succession once each with 50 ml saturated aqueous KHSO$_4$ solution and with saturated aqueous common salt solution, dried over sodium sulfate and the solvent was very largely evaporated at reduced pressure. Drying of the remaining residue in an oil pump vacuum yielded 4.29 g of the title compound as yellowish oil, MS: [M+H]$^+$: 586; m/z: 530; 484; 425.

EXAMPLE 2

2-{[(3S)-1-({[1-(carboxymethyl)-2-oxo-2,3,4,5-tetrahydro-1H-1-benzazepin-3-yl]amino}-carbonyl) cyclopentyl]methyl}-4-(isopropylamino)-4-oxobutyric acid

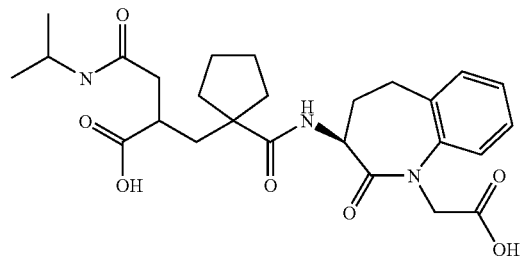

9.97 g of an ethyl 2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}-4-(isopropylamino)-4-oxobutyrate as obtained above under 1E) was dissolved in 200 ml of a water/ethanol mixture (1:1 v/v) and 6.64 g solid NaOH was added thereto with stirring. Stirring was continued over night, the solvent was then very largely evaporated at reduced pressure and the remaining residue was taken up in 100 ml of EA. The aqueous phase was neutralised with saturated aqueous KHSO₄ solution and extracted three times with EA. The combined organic phases were washed with 100 ml saturated aqueous common salt solution and dried over sodium sulfate. Evaporation of the solvent at reduced pressure and drying of the remaining residue in an oil pump vacuum yielded 5.59 g of the title compound.

EXAMPLE 3

(2"rel1")-2-{[(3S)-1-({[1-(carboxymethyl)-2-oxo-2,3,4,5-tetrahydro-1H-1-benzazepin-3-yl]amino}-carbonyl)cyclopentyl]methyl}-4-(isopropylamino)-4-oxobutyric acid

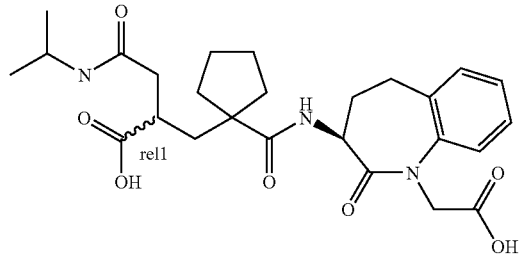

400 mg of the diastereomer mixture obtained above in Example 2) was separated by HPLC in accordance with the procedure set forth below:

Column: LC80-1, 25×8 cm; stationary phase: Chiralpak-kAD, 20μ; mobile phase: heptane/isopropanol 85:15 (v/v)+ 0.1% v/v trifluoroacetic acid (=TFA); UV detection; flow rate: 1 ml/min.; cycle time: 15 minutes;

Analysis: column: DAICEL Chiralpak AD; length: 250 mm; diameter: 4.6 mm; mobile phase: n-heptane 800 ml, 2-propanol 200 ml, TFA 2 ml; flow rate: 0.8 ml/min.; analysis time: 30 minutes. With a retention time of 13.5 min., there was obtained under these conditions 130 mg of the first stereoisomer (=title compound), which was assigned the designation "rel1" in relation to the chiral center "*$C_a$" bearing the group "—COOR¹", as white solid, which precipitated from EE; ¹H-NMR (methanol): 7.37-7.2, m, [4]; 4.76, 4.71, 4.43, 4.38, AB-Q.; 4.4, m, [1]; 3.90, m, [1]; 3.40, m, [1]; 2.22-2.60, m, [2]; 2.48-2.0, m, [12]; 1.10, d, [6]; [a]D=−90° (0.5% in methanol); Mp.: 145° C. With a retention time of 16.2 min., there was obtained under these conditions the second stereoisomer, which was assigned the designation "rel2" in relation to the chiral center "*$C_a$" bearing the group "—COOR¹".

EXAMPLE 4

{(3S)-3-[({1-[(2"rel1")-2-ethoxycarbonyl)-4-(isopropylamino)-4-oxobutyl]cyclopentyl}-carbonyl)amino]-2-oxo-2,3,4,5-tetrahydro-1H-1-benzazepin-1-yl}acetic acid

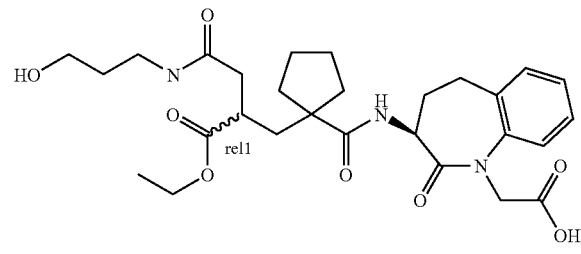

4.29 g ethyl (2"rel1")-2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}-4-(isopropylamino)-4-oxo-butyrate (prepared analogously to Example 1, but with the (2"rel1")-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-ethoxy-4-oxobutyric acid obtained by HPLC separation being used as intermediate product of stage 1E), was dissolved in 30 ml dichloromethane and 17 ml of TFA was added. The mixture was left to stand overnight and the solvent and excess TFA were evaporated at reduced pressure. The remaining residue was taken up in 100 ml EA and the organic phase was washed with water until it became pH-neutral. The organic phase was dried over sodium sulfate and then the solvent was very largely evaporated at reduced pressure. 30 ml toluene in each case was added twice to the residue and the mixture was again evaporated at reduced pressure. Drying of the remaining residue in an oil pump vacuum yielded 2.8 g of the title compound as white foam; ¹H-NMR (CDCl₃): 7.33, m, [4]; 6.82, d, [1]; 5.86, d, [1]; 4.64, m, [1]; 4.54, 4.50, 4.46, 4.42, AB-Q.; 3.20, m, [1]; 1.23, [3]; 1.09, [6]; [a]_D: −155° (1% in methanol).

EXAMPLE 5

Ethyl (2"rel1")-2-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-[(3-hydroxypropyl)amino]-4-oxobutyrate

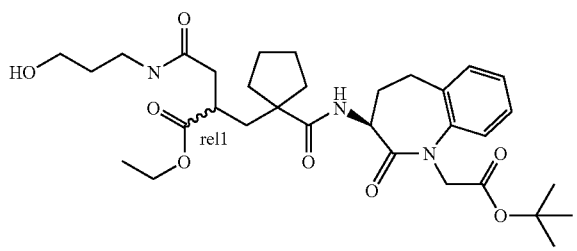

4.2 g (2"rel1")-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-ethoxy-4-oxobutyric acid (preparation of the diastereomer mixture in accordance with Example 1E) and subsequent separation of the diastereomers by means of HPLC) was dissolved in 30 ml dichloromethane. 1.17 ml 3-amino-1-propanol, 235 mg dimethylaminopyridine and 1.61 g EDC were added to this receiving solution with stirring. After 1 h, the mixture was largely evaporated at reduced pressure, the remaining residue was taken up in 100 ml EA and the organic phase was shaken out twice with 30 ml dilute aqueous KHSO₄ solution each time. The organic phase was washed twice more with 30 ml saturated aqueous common salt solution each time, dried over sodium sulfate and the solvent was then largely evaporated at reduced pressure. Drying of the remaining residue in an oil pump vacuum yielded 4 g of the title compound as white foam resin, MS: [M+H]⁺: 602; m/z: 546, 500, 425; ¹H-NMR (CDCl₃): 7.32-7.18, m, [3]; 7.12, d, [2]; 6.63, d, [1]; 6.49, tr, [1]; 4.57, 4.63, 4.34, 4.30, AB-Q. [2]; 4.51, m, [1]; 4.11, m, [2]; 3.57, tr, [2].

EXAMPLE 6

Ethyl (2"rel1")-4-{[3-(acetyloxy)propyl]amino}-2-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-oxobutyrate

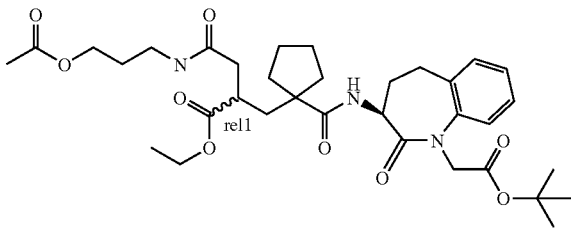

1 g of the ethyl (2"rel1")-2-{[1-({[(3S)-1-(2-tert. butoxy-2-oxoethyl)-2-oxo-2,3,4,5-tetrahydro-1H-1-benzazepin-3-yl]amino]}carbonyl)cyclopentyl]methyl}-4-[(3-hydroxypropyl)-amino-4-oxobutyrate obtained above in Example 5 was dissolved in 20 ml dichloromethane and 340 µl acetyl chloride was added thereto. After 90 minutes, the solvent was largely evaporated at reduced pressure and the remaining residue was taken up in 20 ml EA and washed with 10 ml of a dilute aqueous sodium bicarbonate solution. Then it was dried over magnesium sulfate, the solvent was largely evaporated at reduced pressure and the remaining residue was chromatographed on silica gel (mobile phase: EA/n-hexane 7:3 v/v). Drying the product fractions in an oil pump vacuum ($5 \times 10^{-2}$ mbar) yielded 920 g of the title compound as colourless oil; MS: [M+H]: 644; m/z: 588, 542, 482, 425.

EXAMPLE 7

{(2"rel1")-3-[({1-[(3S)-4-{[3-(acetyloxy)propyl]amino}-2-(ethoxycarbonyl)-4-oxobutyl]cyclopentyl}carbonyl)amino]-2-oxo-2,3,4,5-tetrahydro-1H-1-benzazepin-1-yl}acetic acid

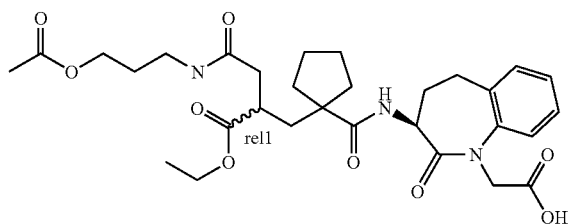

929 mg of the ethyl (2"rel1")-4-{[3-(acetyloxy)propyl]amino}-2-{[1-({[(3S)-1-(2-tert. butoxy-2-oxoethyl)-2-oxo-2,3,4,5-tetrahydro-1H-1-benzazepin-3-yl]amino}carbonyl)-cyclopentyl]methyl}-4-oxobutyrate obtained above in Example 6 was dissolved in 10 ml dichloromethane and 2.2 ml TFA was added thereto. The mixture was left to stand overnight, the solvent was then largely evaporated at reduced pressure and the remaining residue was taken up in 30 ml EA. The organic phase was washed with water until it became pH neutral, was again largely evaporated at reduced pressure and the remaining residue was fumed off twice with 10 ml toluene each time. 750 mg of the title compound was obtained as a white foam resin, MS: [M+H]: 588; m/z: 542, 482, 425; $^1$H-NMR (CDCl$_3$): 7.33-7.14, m, [4]; 6.67, d, [1]; 6.59, tr, [1]; 4.69, 4.64, 4.35, 4.30, AB-Q., [2]; 4.63, m, [1]; 4.17, m, [1]; 4.09, q, [2]; 3.33, m, [1]; 3.15, m, [2].

EXAMPLE 8

((3S)-3-{[(1-{(2"rel1")-2-ethoxycarbonyl)$_4$-[(3-hydroxypropyl)amino]-4-oxobutyl]cyclopentyl}-carbonyl)amino]-2-oxo-2,3,4,5-tetrahydro-1H-1-benzazepin-1-yl}acetic acid

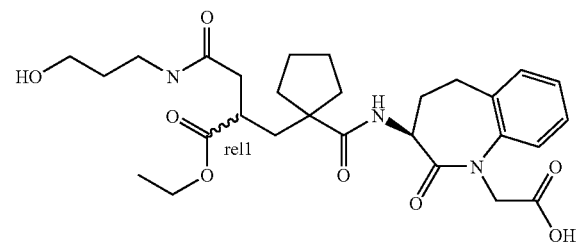

580 mg ethyl (2"rel1")-2-{[1-({[(3S)-1-(2-tert. butoxy-2-oxoethyl)-2-oxo-2,3,4,5-tetrahydro-1H-1-benzazepin-3-yl]amino]}carbonyl)cyclopentyl]methyl}-4-[(3-hydroxypropyl)amino-4-oxobutyrate (for preparation see Example 5) was reacted with TFA in accordance with the method set forth above in Example 4. After purification of the resulting crude product by column chromatography (stationary phase: silica gel; mobile phase: EA/methanol 9:1 (v/v)), 240 mg of the title compound was obtained as colourless resin, $^1$H-NMR (CDCl$_3$): 7.34-7.15, m, [4]; 6.76, tr, [1]; 6.61, d, [1]; 4.75, 4.71, 4.20, 4.16, AB-Q., [2]; 4.57, m, [1]; 4.09, q, [2]; MS: [M+H]$^+$: 546; [α]$_D$=−112.5° (1% in methanol).

EXAMPLE 9

2-{[1-({[(3S)-1-(carboxymethyl)-2-oxo-2,3,4,5-tetrahydro-1H-1-benzazepin-3-yl]amino}-carbonyl)cyclopentyl]methyl}-4-[(3-hydroxypropyl)amino]-4-oxobutyric acid

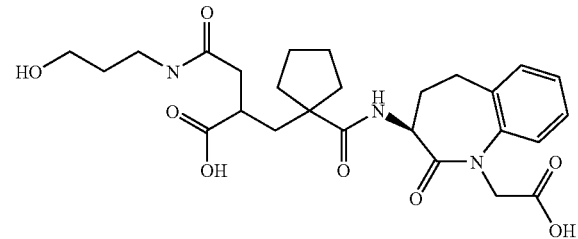

6.43 g ethyl (2"rel1")-2-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-[(3-hydroxypropyl)amino]-4-oxobutyrate (for preparation see Example 5) was dissolved in 140 ml of a 1:1 (v/v) mixture of water and ethanol, and 4.28 g solid NaOH was added thereto with stirring. After 15 h, the solvent was evaporated at reduced pressure, the residue was taken up in 100 ml EA and washed once with 50 ml aqueous KHSO$_4$ solution. The aqueous phase was extracted twice with 30 ml EA each time. The combined organic phases were washed twice with 30 ml aqueous common salt solution each time and dried over sodium sulfate. Evaporation of the solvent yielded 5.41 g of the title compound.

EXAMPLE 10

(2"rel1")-2-{[1-({[(3S)-1-(carboxymethyl)-2-oxo-2, 3,4,5-tetrahydro-1H-1-benzazepin-3-yl] amino}carbonyl)cyclopentyl]methyl}-4-[(3-hydroxypropyl)amino]-4-oxobutyric acid

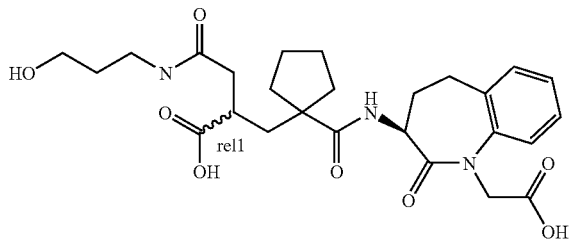

800 mg of the isomer mixture obtained above in Example 9 was separated by preparative HPLC in accordance with the procedure set forth below:

Stationary phase: Nucleosil 100-10; column: 250 mm long, 20 mm diameter; flow rate: 8 ml/min.; mobile phase: n-heptane (800 ml), 2-propanol (200 ml), TFA (1 ml).

Analysis: stationary phase: EC 250/4 Nucleosil 100-10; column 250 ml long, 4 mm diameter, flow rate: 1.5 ml/min.; mobile phase: n-heptane (800 ml), 2-propanol (200 ml), TFA (1 ml). With a retention time of 7.89 min., there was obtained under these conditions 200 mg of the first stereoisomer (=title compound), which was assigned the designation "rel1" in relation to the chiral center "*Ca" bearing the group "—COOR[1]", $^1$H-NMR (CD$_3$OD): 7.38, m, [4]; 4.78, 4.73, 4.43, 4.38, AB-Q., [2]; 4.41, m, [1]; 3.93, m, [1]; 3.56, tr [2]; 3.40, m, [1]; 3.31, m, [1]; 3.22, m, [2]; 2.78, m, [1]; 2.65, m, [1].

With a retention time of 4.47 min., there was obtained under these conditions the second stereoisomer, which was assigned the designation "rel2" in relation to the chiral center "*Ca" bearing the group "—COOR[1]".

EXAMPLE 11

2-{[1-({[(3S)-1-(2-ethoxy-2-oxoethyl)-2-oxo-2,3,4, 5-tetrahydro-1H-1-benzazepin-3-yl]amino}carbonyl) cyclopentyl]methyl}-4-[(3-hydroxypropyl)amino]-4-oxobutyric acid

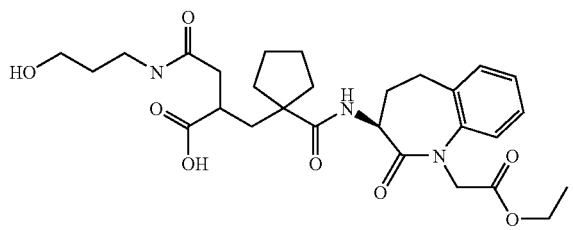

800 mg of the 2-{[1-({[(3S)-1-(carboxymethyl)-2-oxo-2, 3,4,5-tetrahydro-1H-1-benzazepin-3-yl]amino}carbonyl) cyclopentyl]methyl}-4-[(3-hydroxypropyl)amino]-4-oxobutyric acid (isomer mixture) obtained above according to Example 9 was dissolved in 15 ml dimethyl formamide (=DMF). 302.5 mg Cs$_2$CO$_3$ and 169 mg ethyl bromide were added to this receiving solution at room temperature with stirring. After stirring overnight, it was diluted with 42 ml water and 21 ml dichloromethane and the aqueous phase was extracted with dichloromethane. The solvent was largely evaporated at reduced pressure and the remaining residue was chromatographed (stationary phase: silica gel, mobile phase: EA (100%) to EE/MeOH 7:3 (v/v)). Drying the product fractions in an oil pump vacuum (5×10$^{-2}$ mbar) yielded 241 g of the title compound as foam resin, MS: [M+H]+: 546; m/z: 453, 425, 379; $^1$H-NMR (CDCl$_3$): 7.34-7.1, m, [4]; 4.82, 4.77, 4.34, 4.29, AB-Q-. [2]; 3.62, m, [2]; 3.37, m, [3].

EXAMPLE 12

2-{[1-({[(3S)-1-(2-tert. butoxy-2-oxoethyl)-2-oxo-2, 3,4,5-tetrahydro-1H-1-benzazepin-3-yl]amino}-carbonyl)cyclopentyl]methyl}-4-(isopropylamino)-4-oxobutyric acid

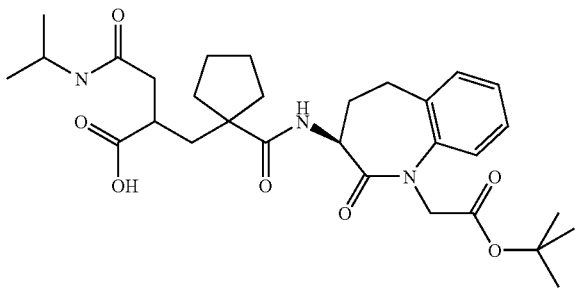

2.6 g ethyl 2-{[(3S)-1-({[1-(2-tert. butoxy-2-oxoethyl)-2-oxo-2,3,4,5-tetrahydro-1H-1-benzazepin-3-yl] amino}carbonyl)cyclopentyl]methyl}-4-(isopropylamino)-4-oxobutyrate (for preparation see Example 1) was dissolved in 52 ml of ethanol. A solution of 710 mg solid NaOH in 52 ml water was added to this receiving solution. After 30 minutes, it was acidulated with dilute aqueous KHSO$_4$ solution to approximately pH 2 and the aqueous phase was extracted three times with 50 ml EA each time. The combined organic phases were dried over magnesium sulfate, the solvent was largely evaporated at reduced pressure and the remaining residue was chromatographed on silica gel (mobile phase: EA/cyclohexane 2:1 v/v). Drying the product fractions in an oil pump vacuum (5×10$^{-2}$ mbar) yielded 2.2 g of the title compound as white foam resin, MS: [M+H]$^+$: 558; m/z: 502, 425, 397, 323.

EXAMPLE 13

4-chlorobenzyl-2-{[1-({[(3S)-1-(2-tert. butoxy-2-oxoethyl)-2-oxo-2,3,4,5-tetrahydro-1H-1-benzazepin-3-yl]amino}-carbonyl)cyclopentyl]methyl}-4-(isopropylamino)$_4$-oxobutyrate

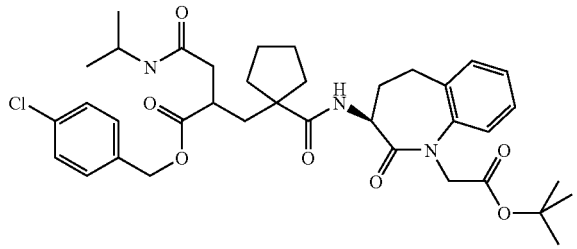

300 mg of the 2-{[1-({[(3S)-1-(2-tert. butoxy-2-oxoethyl)-2-oxo-2,3,4,5-tetrahydro-1H-1-benzazepin-3-yl]amino}-carbonyl)cyclopentyl]methyl}-4-(isopropylamino)$_4$-oxobutyric acid obtained above was dissolved in 5 ml dichloromethane. 33 mg of 4-dimethylaminopyridine (=DMAP), 85 mg 4-chlorobenzyl alcohol and 124 mg EDC×HCl were added thereto and stirring was then carried out overnight. The mixture was diluted with 5 ml dichloromethane and the organic phase was washed in succession once each with 2 ml dilute aqueous KHSO$_4$ solution and with saturated aqueous common salt solution. The organic phase was dried over magnesium sulfate, the solvent was largely evaporated to dryness at reduced pressure and the remaining residue was chromatographed on silica gel (mobile phase: EA/cyclohexane 3:2 v/v). Drying the product fractions in an oil pump vacuum (5×10$^{-2}$ mbar) yielded 320 g of the title compound as white foam; MS: [M+H]$^+$: 682/684; m/z: 626/628, 576, 484, 425.

EXAMPLE 14

{(3S)-3-[({1-[2-{[(4-chlorobenzyl)oxy]carbonyl}-4-(isopropylamino)-4-oxobutyl]cyclopentyl}carbonyl)amino]-2-oxo-2,3,4,5-tetrahydro-1H-1-benzazepin-1-yl}acetic acid

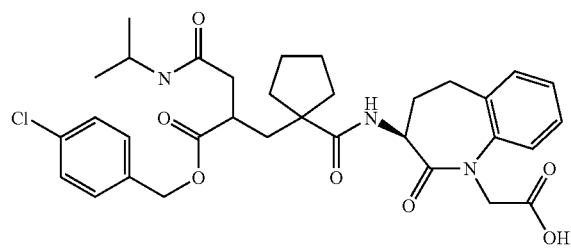

318 g of the 4-chlorobenzyl-2-{[1-({[(3S)-1-(2-tert. butoxy-2-oxoethyl)-2-oxo-2,3,4,5-tetrahydro-1H-1-benzazepin-3-yl]amino}-carbonyl)cyclopentyl]methyl}-4-(isopropylamino)-4-oxobutyrate obtained above was dissolved in 11 ml dichloromethane, 1.08 ml TFA was added thereto and the mixture was stirred overnight. Then the solvent was largely evaporated at reduced pressure, the remaining residue was taken up in 10 ml EA and the organic phase was washed with water until it became pH-neutral. Then the solvent was evaporated again at reduced pressure and the remaining residue was fumed off once with 5 ml of toluene. 305 mg of the title compound was obtained as a white foam resin, MS: [M+H]$^+$: 626/628; m/z: 657, 484, 425.

EXAMPLE 15

(2-methoxyethoxy)methyl-2-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-(isopropylamino)-4-oxobutyric acid

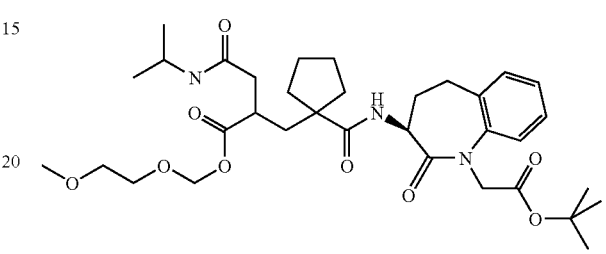

300 mg 2-{[1-({[(3S)-1-(2-tert. butoxy-2-oxoethyl)-2-oxo-2,3,4,5-tetrahydro-1H-1-benzazepin-3-yl]amino}-carbonyl)cyclopentyl]methyl}-4-(isopropylamino)-4-oxobutyric acid (for preparation see Example 12) was dissolved in 5 ml dichloromethane. 33 mg DMAP, 74 μl methoxyethoxymethyl chloride and 90 μl triethylamine were added to this receiving solution. The reaction mixture was stirred overnight, then diluted with 5 ml dichloromethane and the organic phase was washed in succession once each with 3 ml dilute aqueous KHSO$_4$ solution and saturated aqueous common salt solution. The organic phase was dried over magnesium sulfate, the solvent was largely evaporated at reduced pressure and the remaining residue was chromatographed on silica gel (mobile phase: EA/cyclohexane 2:1 v/v). Drying the product fractions in an oil pump vacuum yielded 191 g of the title compound, MS: [M+H]$^+$: 646; m/z: 590, 540, 484, 425.

EXAMPLE 44

Ethyl (2"rel1")-2-{[1-({[(3S)-1-(2-ethoxy-2-oxoethyl)-2-oxo-2,3,4,5-tetrahydro-1H-1-benzazepin-3-yl]amino}carbonyl)cyclopentyl]methyl}-4-[(3-hydroxypropyl)amino]-4-oxobutyrate

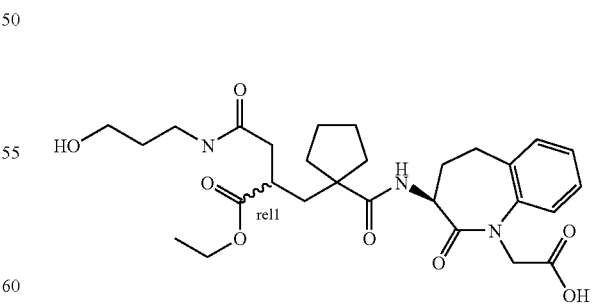

140 mg (2"rel1")-2-{[1-({[(3S)-1-(carboxymethyl)-2-oxo-2,3,4,5-tetrahydro-1H-1-benzazepin-3-yl]amino}carbonyl)cyclopentyl]methyl}-4-[(3-hydroxypropyl)-amino]-4-oxobutyrate acid (for preparation see Example 10) was dissolved in 3 ml ethanol, 5 drops of conc.

sulfuric acid were added thereto and the mixture was stirred for 2 days at room temperature. Then the solvent was largely removed at reduced pressure and the remaining residue was taken up in 5 ml EA. The organic phase was washed twice with 2 ml aqueous NaHSO$_4$ solution each time. After drying over sodium sulfate, the solvent was distilled off at reduced pressure and the residue was chromatographed on silica gel (mobile phase: EA/cyclohexane 8:2 (v/v)). 46 mg of the title compound was obtained as a white foam; MS: [M+H]$^+$: 574; m/z: 528, 323; $^1$H-NMR (CDCl$_3$): 7.33-7.11, m, [4]; 6.69, m, [1]; 6.44, m, [1]; 4.79, 4.75, 4.34, 4.30, AB-Q-. [2]; 4.48, m, [1].

The compounds of Formula I listed in the following Table 9 can also be prepared according to the processes described in the examples above or in a manner analogous to said processes.

TABLE 9

Further compounds of Formula I

| Ex. No. | R$^1$ | R$^2$ | R$^3$ | R$^4$ | Config. C$_a$* | Config. C$_b$* | [M + H]$^+$ |
|---|---|---|---|---|---|---|---|
| 16 | H | H | methoxyethyl | H | rac | S | 518 |
| 17 | H | H | 3-(2-oxoazepanyl) | H | rac | S | 571 |
| 18 | ethyl | | —(CH$_2$)$_2$—O—(CH$_2$)$_2$— | H | rac | S | 558 |
| 19 | H | | —(CH$_2$)$_2$—O—(CH$_2$)$_2$— | H | rel1 | S | |
| 20 | H | H | 4-methoxyphenyl-2-oxoethyl | H | rac | S | 608 |
| 21 | H | H | 3-oxo-1,1-dimethylbutyl | H | rac | S | 558 |
| 22 | H | H | phenyl-2-oxoethyl | H | rac | S | 578 |
| 23 | H | H | cyclopropylmethyl | H | rac | S | 514 |
| 24 | H | H | 4-methoxybenzyl | H | rac | S | 580 |
| 25 | H | H | 4-methoxyphenyl-ethyl | H | rac | S | 594 |
| 26 | H | H | 2-methoxybenzyl | H | rac | S | 580 |
| 27 | H | H | benzyl | H | rac | S | 550 |
| 28 | H | H | methyl | H | rac | S | 474 |
| 29 | ethyl | H | 2-(4-methoxy-phenyl)-2-oxoethyl | H | rac | S | 636 |
| 30 | ethyl | H | methoxyethyl | H | rel1 | S | 546 |
| 31 | H | H | 2-methoxybenzyl | H | rac | S | 580 |
| 32 | H | methyl | isopropyl | H | rac | S | 516 |
| 33 | ethyl | H | 3,4-dimethoxy-benzyl | H | rac | S | 638 |
| 34 | ethyl | H | cyclopropyl | H | rac | S | 528 |
| 35 | ethyl | H | 2-hydroxyethyl | H | rac | S | 532 |
| 36 | ethyl | H | 4-methoxybenzyl | H | rac | S | 608 |
| 37 | ethyl | H | 1-naphthylmethyl | H | rac | S | 628 |
| 38 | ethyl | H | 4-methoxyphenyl-ethyl | H | rac | S | 622 |
| 39 | isopropyl | H | isopropyl | H | rac | S | 544 |
| 40 | n-butyl | H | isopropyl | H | rac | S | 558 |
| 41 | H | H | isopropyl | methoxy-ethoxy-methyl | rac | S | 590 |
| 42 | 2-chloro-benzyl | H | isopropyl | H | rac | S | 627 |
| 43 | H | methyl | 2-hydroxyethyl | H | rac | S | 518 |
| 44 | | | see above | | | | |
| 45 | H | | —(CH$_2$)$_2$—CO—(CH$_2$)$_2$— | H | rac | S | 542 |
| 46 | ethyl | | —(CH$_2$)$_2$—CO—(CH$_2$)$_2$— | H | rac | S | 570 |
| 47 | ethyl | | —(CH$_2$)$_2$—N(Bn)—(CH$_2$)$_2$— | H | rac | S | 647 |
| 48 | ethyl | | —(CH$_2$)$_2$—S—(CH$_2$)$_2$— | H | rac | S | 574 |
| 49 | H | | —(CH$_2$)$_4$— | H | rac | S | 514 |
| 50 | H | | —(CH$_2$)$_3$—CH(CH$_2$—OH)—CH$_2$— | H | rac | S | 558 |
| 51 | H | methyl | —CH$_2$—(CHOH)—CH$_2$OH | H | rac | S | 548 |
| 52 | H | ethyl | —(CH$_2$)$_3$—NH—C$_2$H$_5$ | H | rac | S | 573 |
| 53 | ethyl | 2-hydroxy-ethyl | 2-hydroxyethyl | H | rac | S | 576 |
| 54 | H | methyl | methyl | H | rac | S | 488 |
| 55 | H | ethyl | ethyl | H | rac | S | 516 |
| 56 | H | methyl | 3-hydroxypropyl | H | rac | S | 532 |
| 57 | H | | —(CH$_2$)$_2$—CH(OH)—(CH$_2$)$_2$— | H | rac | S | 544 |
| 58 | H | 2-hydroxy-ethyl | 2-hydroxyethyl | H | rac | S | 548 |
| 59 | H | methyl | —(CH$_2$)$_2$—N(CH$_3$)$_2$ | H | rel1 | S | 545 |
| 60 | H | methyl | —(CH$_2$)$_3$—N(CH$_3$)$_2$ | H | rac | S | 559 |
| 61 | ethyl | | —(CH$_2$)$_2$—CH(—O-valine)-(CH$_2$)$_2$— | H | rac | S | 671 |
| 62 | ethyl | methyl | —(CH$_2$)$_3$—O-valine | H | rac | S | 659 |
| 63 | H | methyl | isopropyl | H | rel1 | S | 516 |
| 64 | H | methyl | —(CH$_2$)$_3$—N(CH$_3$)$_2$ | H | rel1 | S | 559 |
| 65 | H | methyl | —(CH$_2$)$_3$—NH$_2$ | H | rac | S | 531 |
| 66 | H | | —(CH$_2$)—O—(CH$_2$)$_2$ | H | rac | S | 530 |

TABLE 9-continued

Further compounds of Formula I

| Ex. No. | R¹ | R² | R³ | R⁴ | Config. $C_a$* | Config. $C_b$* | [M + H]⁺ |
|---|---|---|---|---|---|---|---|
| 67 | H | ethyl | —(CH$_2$)$_3$—NH$_2$ | H | rac | S | 545 |
| 68 | H | methyl | —(CH$_2$)$_2$—NH(CH$_3$) | H | rac | S | 531 |
| 75 | H | methyl | —(CH$_2$)$_4$—NH$_2$ | H | rac | S | 545 |
| 76 | H | ethyl | —(CH$_2$)$_4$—NH$_2$ | H | rac | S | 559 |
| 77 | H | methyl | —(CH$_2$)$_3$—NH(CH$_3$) | H | rac | S | 545 |
| 78 | H | methyl | —(CH$_2$)$_5$—NH$_2$ | H | rac | S | |
| 79 | H | ethyl | —(CH$_2$)$_5$—NH$_2$ | H | rac | S | | rac = racemic;
Bn = benzyl

EXAMPLE 69

Tert. butyl 2-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-(4-hydroxypiperidin-1-yl)-4-oxobutanoate

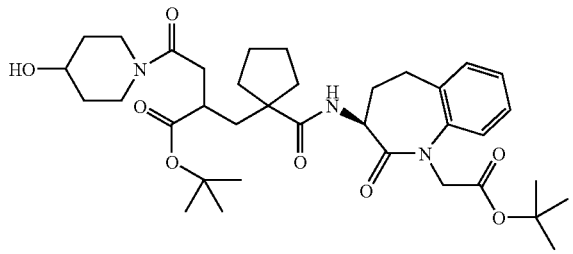

A) 100 g of 2-[(2-benzyloxy)-2-oxoethyl]acrylic acid (for production see example 1A) was reacted with 47 ml of thionyl chloride, 43 ml of tert. butanol and 110 ml of pyridine according to the procedure described in example 1B) to yield 69.8 g of 2-methylenesuccinic acid-4-benzylester-1-tert. butylester, [M+H]⁺: 277.

B) 29.6 g of 2-methylenesuccinic acid-4-benzylester-1-tert. butylester as obtained above was reacted with 41.4 ml of diisopropylamine, 200 ml of a 1.6 M solution of n-butyllithium in n-hexane and 12 ml of cyclopentanecarboxylic acid according to the procedure described in example 1C) to yield 24.5 g of 1-[4-(benzyloxy)-2-(tert. butoxycarbonyl)-4-oxobutyl]cyclopentanecarboxylic acid.

C) 15.8 g of 1-[4-(benzyloxy)-2-(tert. butoxycarbonyl)-4-oxobutyl]cyclopentane-carboxylic acid as obtained above was reacted with 11.75 g of tert. butyl-[(3S)-3-amino-2-oxo-2,3,4,5-tetrahydro)-1H-benzazepin-1-yl]acetate (for production see EP 0 733 642 A1) according to the procedure described in example 1D) to yield 21 g of 2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}succinic acid-4-benzylester-1-tert. butylester.

D) 21 g of 2-{[(3S)-1-({[1-(2-tert. butoxy-2-oxoethyl)-2-oxo-2,3,4,5-tetrahydro-1H-1-benzazepin-3-yl]amino}carbonyl)cyclopentyl]methyl}succinic acid-4-benzylester-1-tert. butylester as obtained above was treated with 6 g of palladium on activated carbon and hydrated for 12 hours and a hydrogen pressure of 1.3 bar according to the procedure described in example 1E) to yield 10 g of 4-tert. butoxy-3-{[1-({[(3S)-1-(2-tert. butoxy-2-oxoethyl)-2-oxo-2,3,4,5-tetrahydro-1H-1-benzazepin-3-yl]amino}-carbonyl)cyclopentyl]methyl}-4-oxobutanoic acid; MS: [M+H]⁺: 573; m/z: 517, 461; ¹H-NMR (CDCl$_3$): 7.31-7.17, m, [3]; 7.10, m, [1]; 6.80, d, [0.5]; 6.72, d, [0.5]; 4.60-4.30, m, [3]; 3.30, m, [0.5]; 3.17, m, [0.5].

E) 1.11 g of 4-tert. butoxy-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-oxobutanoic acid as obtained above was dissolved in 7.8 ml of dichloromethane and 300 µl of triethylamine was added. After cooling to 0° C. in an ice bath, 222 µl of ethylchloroformate was added dropwise to this receiving solution. The mixture was allowed to stir for 30 minutes, then 216 mg of 4-hydroxypiperidine was added and the mixture was stirred over night. The mixture was diluted with EA and washed with aqueous KHSO$_4$— solution and with brine. Drying of the organic layer over magnesium sulfate and column chromatography on silica gel (liquid phase: EA/cyclohexane 1:1(v/v) changed to pure EA changed to EA/methanol 4:1 (v/v)) yielded 550 mg of the title compound as a white foam, MS: [M+H]⁺: 656; m/z: 425, 397, 323.

EXAMPLE 70

2-{[1-({[1-(carboxymethyl)-2-oxo-2,3,4,5-tetrahydro-1H-1-benzazepin-3-yl]amino}-carbonyl)cyclopentyl]methyl}-4-oxo-4-[4-(L-valyloxy)piperidin-1-yl]butanoic acid

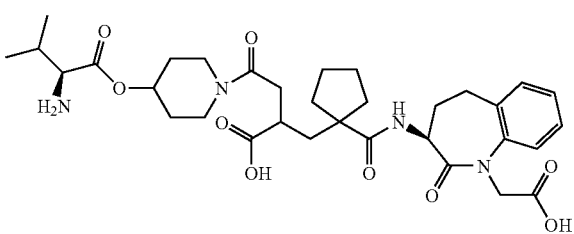

A) 548 mg of tert. butyl 2-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-(4-hydroxypiperidin-1-yl)-4-oxobutanoate as obtained in example 69 was dissolved in 3 ml of dichloromethane. Then 51 mg of DMAP, 182 mg of BOC-L-valine and 176 mg of EDC were added. After stirring for 3 hours the mixture was diluted with EA and consecutively washed with aqueous KHSO₄ solution and with brine. Drying of the organic layer over magnesium sulfate and column chromatography on silica gel (liquid phase: EA/cyclohexane 1:1 (v/v) changed to pure EA) yielded 551 mg of 1-(4-tert. butoxy-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-oxobutanoyl)piperidin-4-yl-N-(tert. butoxycarbonyl)-L-valinate, MS: [M+H]⁺: 855; m/z: 699, 643, 625, 425, 397, 323, 235.

B) 551 mg of 1-(4-tert. butoxy-3-{[1-({[(3S)-1-(2-tert. butoxy-2-oxoethyl)-2-oxo-2,3,4,5-tetrahydro-1H-1-benzazepin-3-yl]amino}carbonyl)cyclopentyl]methyl}-4-oxobutanoyl)piperidin-4-yl-N-(tert. butoxycarbonyl)-L-valinate as obtained above was dissolved in 14 ml of dichloromethane and 1.49 ml of trifluoroacetic acid was added to this receiving solution. After stirring over night the solvent and excess of acid were evaporated at reduced pressure. EA was added to the remaining residue and the organic layer was washed with an aqueous saturated sodium bicarbonate solution until a pH of 4 was reached. The aqueous layer was then extracted thrice with EA and the combined organic layers were dried over magnesium sulfate. Evaporation of the solvent at reduced pressure and subsequent drying of the remaining residue in an oil pump vacuum yielded 310 mg of the title compound as a white foam, MS: [M+H]: 643; m/z: 425, 397, 323.

EXAMPLE 71

Tert. butyl 2-{[1-({[(3S)-1-(2-ethoxy-2-oxoethyl)-2-oxo-2,3,4,5-tetrahydro-1H-1-benzazepin-3-yl]amino}carbonyl)cyclopentyl]methyl}-4-[isopropyl(methyl)amino]-4-oxo-butanoate

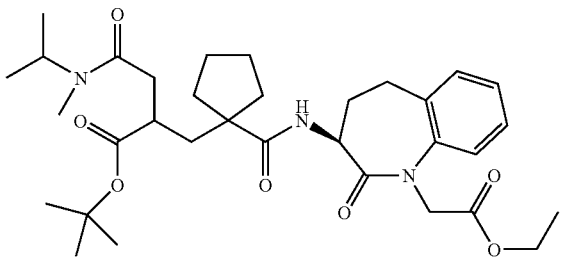

A) 20 g of 1-[4-(benzyloxy)-2-(tert. butoxycarbonyl)-4-oxobutyl]cyclopentanecarboxylic acid (for preparation see example 69B)) was reacted with 13.4 g of ethyl-[(3S)-3-amino-2-oxo-2,3,4,5-tetrahydro)-1H-benzazepin-1-yl] acetate (preparation analogous to methods described in EP 0 733 642 A1) according to the procedure described in example 1D) to yield 28.6 g of 4-benzyl-1-tert. butyl-2-{[1-({[(3S)-1-(2-ethoxy-2-oxoethyl)-2-oxo-2,3,4,5-tetrahydro-1H-1-benzazepin-3-yl]amino}carbonyl)-cyclopentyl]methyl}succinate.

B) 28.6 g of 4-benzyl-1-tert. butyl-2-{[1-({[(3S)-1-(2-ethoxy-2-oxoethyl)-2-oxo-2,3,4,5-tetrahydro-1H-1-benzazepin-3-yl]amino}carbonyl)cyclopentyl] methyl}succinate as obtained above was treated with 5 g of palladium on activated carbon and hydrogenated for 4.5 hours and a hydrogen pressure of 2.3 bar according to the procedure described in example 1E) to yield 16 g of 4-tert. butoxy-3-{[1-({[(3S)-1-(2-ethoxy-2-oxoethyl)-2-oxo-2,3,4,5-tetrahydro-1H-1-benzazepin-3-yl] amino}carbonyl)cyclopentyl]methyl}-4-oxobutanoic acid, [M+H]⁺: 545; m/z: 489.

C) 3 g of 4-tert. butoxy-3-{[1-({[(3S)-1-(2-ethoxy-2-oxoethyl)-2-oxo-2,3,4,5-tetrahydro-1H-1-benzazepin-3-yl]amino}carbonyl)cyclopentyl]methyl}-4-oxobutanoic acid as obtained above was reacted with 859 µl methylisopropylamine according to the procedure described in example 1F) to yield 1.6 g of the title compound as a white foam, MS: [M+H]⁺: 600; m/z: 544.

EXAMPLE 72

2-{[1-({[(3S)-1-(2-Ethoxy-2-oxoethyl)-2-oxo-2,3,4,5-tetrahydro-1H-1-benzazepin-3-yl]-amino}carbonyl)cyclopentyl]methyl}4-[isopropyl(methyl)amino]-4-oxobutanoic acid

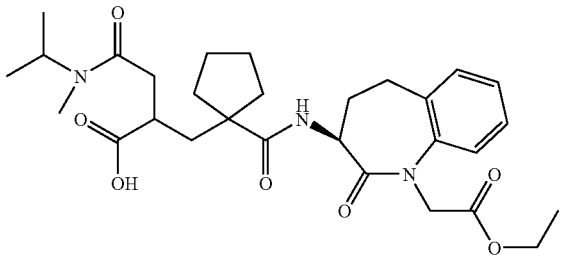

507 mg of tert. butyl 2-{[1-({[(3S)-1-(2-ethoxy-2-oxoethyl)-2-oxo-2,3,4,5-tetrahydro-1H-1-benzazepin-3-yl]amino}carbonyl)cyclopentyl]methyl}-4-[isopropyl(methyl)amino]-4-oxo-butanoate as obtained in example 71 was dissolved in 18 ml of dichloromethane and 1.95 ml of trifluoroacetic acid was added to this receiving solution. After stirring over night the solvent and excess of acid were evaporated at reduced pressure. EA was added to the remaining residue and the organic layer was washed with an aqueous saturated sodium bicarbonate solution, until the aqueous layer reached a pH of 5. The organic layer was then dried over magnesium sulfate. Drying of the organic layer over magnesium sulfate and column chromatography on silica gel (liquid phase: EA/cyclohexane 1:1 (v/v) changed to pure EA) yielded 430 mg of the title compound as a white foam, MS: [M+H]⁺: 544.

EXAMPLE 73

1-[(Ethoxycarbonyl)oxy]ethyl 2-{[1-({[(3S)-1-(2-ethoxy-2-oxoethyl)-2-oxo-2,3,4,5-tetrahydro-1H-1-benzazepin-3-yl]amino}carbonyl)cyclopentyl]methyl}-4-[isopropyl(methyl)-amino]-4-oxobutanoate

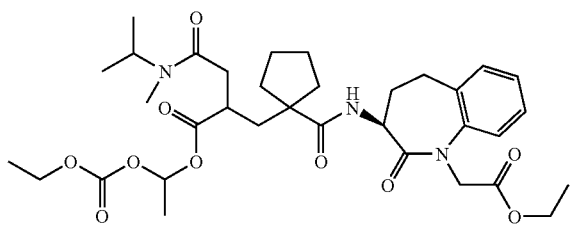

107 mg of 2-{[1-({[(3S)-1-(2-Ethoxy-2-oxoethyl)-2-oxo-2,3,4,5-tetrahydro-1H-1-benzazepin-3-yl]amino}carbonyl)

cyclopentyl]methyl}-4-[isopropyl(methyl)amino]-4-oxobu-
tanoic acid (for preparation see example 72) was dissolved
in 1 ml of DMF. Then 83 μl of triethylamine, 20 mg of solid
K$_2$CO$_3$ and 85 μl of chloroethylethylcarbonate was added.
After stirring over night the mixture was diluted with EA and
consecutively washed with an aqueous KHSO$_4$ solution and
with brine. Drying of the organic layer over magnesium
sulfate and column chromatography on silica gel (liquid
phase: EA/cyclohexane 1:1 (v/v)) yielded 41 mg of the title
compound as a white foam, MS: [M+H]$^+$: 660; m/z: 526,
449, 310, 253.

EXAMPLE 74

1-[(Ethoxycarbonyl)oxy]ethyl 2-{[1-({[(3S)-1-(2-
{1-[(ethoxycarbonyl)oxy]ethoxy}-2-oxo-ethyl)-2-
oxo-2,3,4,5-tetrahydro-1H-1-benzazepin-3-yl]
amino}carbonyl)cyclopentyl]-methyl}-4-[isopropyl
(methyl)amino]-4-oxobutanoate

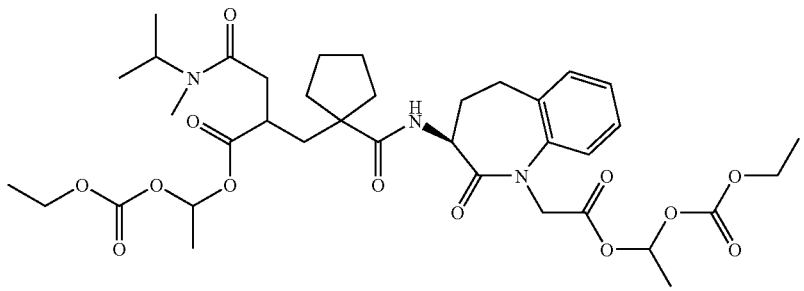

500 mg of ethyl 2-{[1-({[(3S)-1-(2-tert-butoxy-2-oxoet-
hyl)-2-oxo-2,3,4,5-tetrahydro-1H-1-benzazepin-3-yl]
amino}carbonyl)cyclopentyl]methyl}-4-[isopropyl(methyl)
amino]-4-oxo-butanoate (see example 32, synthesis
analogous to example 2) was dissolved in 10 ml of DMF.
Then 312 μl of chloroethylethylcarbonate, 758 mg of solid
Cs$_2$CO$_3$ and 80 mg of solid potassium iodide were added.
After stirring for 5 hours at 60° C. the mixture was diluted
with EA and was then twice washed with water. Drying of
the organic layer over magnesium sulfate and column chro-
matography on silica gel (liquid phase: cyclohexane,
changed to EA/cyclohexane 1:1 (v/v)) yielded 360 mg of the
title compound as a white oil, MS: [M+H]$^+$: 748; m/z: 614,
480.

EXAMPLE I

Capsules Containing {(3S)-3-[({1-[(2"rel1")-2-
ethoxycarbonyl)-4-(isopropylamino)-4-oxobutyl]
cyclopentyl}-carbonyl)amino]-2-oxo-2,3,4,5-tetrahy-
dro-1H-1-benzazepin-1-yl}acetic acid Capsules with the following composition per capsule
were produced:

| | |
|---|---|
| {(3S)-3-[({1-[2'''}-2-ethoxycarbonyl)-4-(isopropyl-amino)-4-oxobutyl]cyclopentyl)-carbonyl)amino]-2-oxo-2,3,4,5-tetrahydro-1H-1-benzazepin-1-yl}-acetic acid | 20 mg |
| Corn starch | 60 mg |

-continued

| | |
|---|---|
| Lactose | 300 mg |
| EA | q.s. |

The active substance, the corn starch and the lactose were
processed into a homogeneous pasty mixture using EA. The
paste was ground and the resulting granules were placed on
a suitable tray and dried at 45° C. in order to remove the
solvent. The dried granules were passed through a crusher
and mixed in a mixer with the further following auxiliaries:

| | |
|---|---|
| Talcum | 5 mg |
| Magnesium stearate | 5 mg |
| Corn starch | 9 mg | and then filled into 400 mg capsules (=capsule size 0).

The foregoing description and examples have been set
forth merely to illustrate the invention and are not intended
to be limiting. Since modifications of the described embodi-
ments incorporating the spirit and substance of the invention
may occur to persons skilled in the art the invention should
be construed broadly to include all variations within the
scope of the appended claims and equivalents thereof.

What is claimed is:
1. A compound corresponding to the formula I:

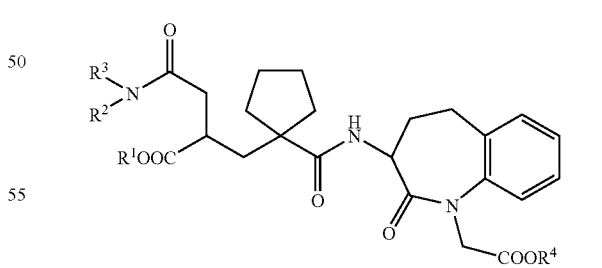

wherein
R$^1$ is hydrogen or a group forming a biolabile ester,
R$^2$ is hydrogen, C$_{1-4}$-alkyl or C$_{1-4}$-hydroxyalkyl, the
hydroxyl group of which is optionally esterified with
C$_{2-4}$-alkanoyl or an amino acid, and
R$^3$ is C$_{1-4}$-alkyl; C$_{1-4}$-alkoxy-C$_{1-4}$-alkyl; C$_{1-4}$-hydroxy-
alkyl, which is optionally substituted by a second
hydroxyl group and the hydroxyl groups of which are each optionally esterified with $C_{2-4}$-alkanoyl or an amino acid; $(C_{0-4}$-alkyl$)_2$amino-$C_{1-6}$-alkyl; $C_{3-7}$-cycloalkyl; $C_{3-7}$-cycloalkyl-$C_{1-4}$-alkyl; phenyl-$C_{1-4}$-alkyl, the phenyl group of which is optionally substituted once or twice by $C_{1-4}$-alkyl, $C_{1-4}$-alkoxy or halogen; naphthyl-$C_{1-4}$-alkyl; $C_{3-6}$-oxoalkyl; phenylcarbonylmethyl, the phenyl group of which is optionally substituted once or twice by $C_{1-4}$-alkyl, $C_{1-4}$-alkoxy or halogen, or 2-oxoazepanyl, or $R^2$ and $R^3$ together are $C_{4-7}$-alkylene, the methylene groups of which are optionally replaced once or twice by carbonyl, nitrogen, oxygen or sulphur, or which are optionally substituted once by hydroxy, which is optionally esterified with $C_{2-4}$-alkanoyl or an amino acid; $C_{1-4}$-alkyl; $C_{1-4}$-hydroxyalkyl, the hydroxyl group of which is optionally esterified with $C_{2-4}$-alkanoyl or an amino acid residue; phenyl or benzyl, and $R^4$ is hydrogen or a group forming a biolabile ester, or a physiologically acceptable salt thereof.

2. A compound according to claim 1, wherein $R^1$ is hydrogen or a group forming a biolabile ester, $R^2$ is hydrogen, $C_{1-4}$-alkyl or $C_{1-4}$-hydroxyalkyl, the hydroxyl group of which is optionally substituted by $C_{2-4}$-alkanoyl, and $R^3$ is $C_{1-4}$-alkyl; $C_{1-4}$-alkoxy-$C_{1-4}$-alkyl; $C_{1-4}$-hydroxyalkyl, which is optionally substituted by a second hydroxyl group and the hydroxyl groups of which are optionally substituted by $C_{2-4}$-alkanoyl; $C_{1-4}$-alkylamino-$C_{1-4}$-alkyl; $C_{3-7}$-cycloalkyl; $C_{3-7}$-cycloalkyl-$C_{1-4}$-alkyl; phenyl-$C_{1-4}$-alkyl, the phenyl group of which is optionally substituted 1-2 times by $C_{1-4}$-alkyl, $C_{1-4}$-alkoxy and/or halogen; naphthyl-$C_{1-4}$-alkyl; $C_{3-6}$-oxoalkyl; phenylcarbonylmethyl, the phenyl group of which is optionally substituted 1-2 times by $C_{1-4}$-alkyl, $C_{1-4}$-alkoxy and/or halogen, or 2-oxoazepanyl, or $R^2$ and $R^3$ together are $C_{4-7}$-alkylene, the methylene groups of which are optionally replaced 1-2 times by carbonyl, nitrogen, oxygen and/or sulfur and which are optionally substituted once by $C_{1-4}$-alkyl; $C_{1-4}$-hydroxyalkyl, the hydroxyl group of which is optionally substituted by $C_{2-4}$-alkanoyl; oxygen; phenyl or benzyl, and $R^4$ is hydrogen or a group forming a biolabile ester, or a physiologically acceptable salt thereof.

3. A compound according to claim 1, wherein $R^1$ is hydrogen, ethyl, methoxyethoxymethyl, (RS)-1-[[(isopropyl)carbonyl]oxy]ethyl, (RS)-1-[[(ethyl)carbonyl]-oxy]-2-methylpropyl, (RS)-1-[[(cyclohexyloxy)carbonyl]oxy]ethyl, 5-methyl-2-oxo-1,3-dioxolen-4-yl-methyl, 2-oxo-1,3-dioxolan-4-yl-methyl or (RS)-1-[[(ethoxy)carbonyl]oxy]-ethyl.

4. A compound according to claim 1, wherein $R^2$ is hydrogen, methyl, ethyl, 2-hydroxyethyl or 3-hydroxypropyl, wherein each hydroxyl group may optionally be esterified with $C_{2-4}$-alkanoyl or an amino acid residue.

5. A compound according to claim 1, wherein $R^3$ is isopropyl; methoxyethyl; 2-hydroxyethyl or 3-hydroxypropyl, each hydroxyl group optionally being esterified with $C_{2-4}$-alkanoyl or an amino acid; 3-acetyloxy-n-propyl; cyclopropylmethyl; 2-methoxybenzyl, 4-methoxybenzyl, 4-methoxyphenylethyl, 2,4-dimethoxybenzyl; 1-naphthylmethyl; 3-oxo-1,1-dimethylbutyl; phenyl-2-oxoethyl, 2-(4-methoxyphenyl)-2-oxoethyl, 3-(2-oxoazepanyl), dimethylamino-n-propyl, (methyl)aminoethyl, amino-n-propyl, amino-n-butyl, and amino-n-pentyl.

6. A compound I according to claim 1, wherein $R^2$ and $R^3$ together are morpholine; piperidine; 4-ketopiperidine; 4-hydroxypiperidine optionally esterified at the hydroxyl group with $C_{2-4}$-alkanoyl or an amino acid residue; piperazine or pyrrolidine.

7. A compound according to claim 1, wherein $R^4$ is hydrogen, $C_{1-4}$-alkyl, p-methoxybenzyl, N,N-di-($C_{0-4}$-alkyl) amino-$C_{1-6}$-alkyl, (RS)-1-[[(isopropyl)carbonyl]oxy]ethyl, (RS)-1-[[(ethyl)carbonyl]oxy]-2-methylpropyl, (RS)-1-[[(cyclohexyloxy)carbonyl]oxy]ethyl, 5-methyl-2-oxo-1,3-dioxolen-4-yl-methyl, 2-oxo-1,3-dioxolan-4-yl-methyl or (RS)-1-[[(ethoxy)carbonyl]oxy]ethyl.

8. A compound according to claim 1, selected from the group consisting of:

2-{[1-({[1-(carboxymethyl)-2-oxo-2,3,4,5-tetrahydro-1H-1-benzazepin-3-yl]amino}-carbonyl)cyclopentyl] methyl}4-[isopropyl(methyl)amino]-4-oxobutanoic acid;

2-{[1-({[1-(carboxymethyl)-2-oxo-2,3,4,5-tetrahydro-1H-1-benzazepin-3-yl]amino}carbonyl)cyclopentyl] methyl}-4-(dimethylamino)-4-oxobutanoic acid;

2-{[1-({[1-(carboxymethyl)-2-oxo-2,3,4,5-tetrahydro-1H-1-benzazepin-3-yl]amino}carbonyl)cyclopentyl] methyl}-4-(diethylamino)-4-oxobutanoic acid;

2-{[1-({[1-(carboxymethyl)-2-oxo-2,3,4,5-tetrahydro-1H-1-benzazepin-3-yl]amino}-carbonyl)cyclopentyl] methyl}-4-[(2-hydroxyethyl)(methyl)amino]4-oxobutanoic acid;

2-{[1-({[1-(carboxymethyl)-2-oxo-2,3,4,5-tetrahydro-1H-1-benzazepin-3-yl]amino}-carbonyl)cyclopentyl] methyl}-4-[(3-hydroxypropyl)(methyl)amino]-4-oxobutanoic acid;

2-{[1-({[1-(carboxymethyl)-2-oxo-2,3,4,5-tetrahydro-1H-1-benzazepin-3-yl]amino}-carbonyl)cyclopentyl] methyl}-4-(4-hydroxypiperidin-1-yl)-4-oxobutanoic acid;

2-{[1-({[1-(carboxymethyl)-2-oxo-2,3,4,5-tetrahydro-1H-1-benzazepin-3-yl]amino}-carbonyl)cyclopentyl] methyl}-4-oxo-4-[4-(L-valyloxy)piperidin-1-yl]butanoic acid;

2-{[1-({[1-(carboxymethyl)-2-oxo-2,3,4,5-tetrahydro-1H-1-benzazepin-3-yl]amino}-carbonyl)cyclopentyl] methyl}4-morpholin-4-yl-4-oxobutanoic acid;

2-{[1-({[1-(carboxymethyl)-2-oxo-2,3,4,5-tetrahydro-1H-1-benzazepin-3-yl]amino}-carbonyl)cyclopentyl] methyl}-4-oxo-4-(4-oxopiperidin-1-yl)butanoic acid;

4-[bis(2-hydroxyethyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid;

2-{[1-({[1-(carboxymethyl)-2-oxo-2,3,4,5-tetrahydro-1H-1-benzazepin-3-yl]amino}-carbonyl)cyclopentyl] methyl}-4-{ethyl[3-(ethylamino)propyl]amino}-4-oxobutanoic acid, 2-{[1-({[1-(carboxymethyl)-2-oxo-2,3,4,5-tetrahydro-1H-1-benzazepin-3-yl]amino}-carbonyl)cyclopentyl] methyl}-4-[[2-(dimethylamino)ethyl](methyl)amino]-4-oxobutanoic acid, 4-[(3-aminopropyl)(ethyl)amino]-2-{[1-({[1-(carboxymethyl)-2-oxo-2,3,4,5-tetrahydro-1H-1-benzazepin-3-yl]amino}carbonyl)cyclopentyl]methyl}4-oxobutanoic acid, 2-{[1-({[1-(carboxymethyl)-2-oxo-2,3,4,5-tetrahydro-1H-1-benzazepin-3-yl]amino}-carbonyl)cyclopentyl] methyl}-4-{methyl[2-(methylamino)ethyl]amino}-4-oxobutanoic acid, 4-[(4-aminobutyl)(methyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid, 4-[(4-aminobutyl)(ethyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid, 2-{[1-({[1-(carboxymethyl)-2-oxo-2,3,4,5-tetrahydro-1H-1-benzazepin-3-yl]amino}-carbonyl)cyclopentyl]methyl}-4-{methyl[3-(methylamino)propyl]amino}-4-oxobutanoic acid, 2-[1-1-(carboxymethyl)-2-oxo-2,3,4,5-tetrahydro-1H-benzo[b]azepin-3-ylcarbamoyl)cyclopentylmethyl]-N-(3-dimethylamino-propyl)-N-methyl-succinamic acid, and 4-[(5-aminopentyl)(methyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid, or a biolabile ester or physiologically acceptable salt thereof.

9. A compound according to claim 1, wherein the chiral carbon atom bearing the amide side chain in position 3 of the benzazepine skeleton is in the "S" configuration.

10. A pharmaceutical composition comprising a compound according to claim 1, and at least one pharmaceutical carrier or excipient.

11. A method of treating or inhibiting a cardiovascular disorder or disease in a patient, wherein said cardiovascular disorder or disease is selected from the group consisting of congestive heart failure, and primary and secondary hypertension, and said method comprises administering to said patient a pharmaceutically effective amount of a compound according to claim 1.

12. A method of treating or inhibiting an adverse condition associated with apoptosis in a patient, wherein said adverse condition is a neurodegenerative disorder selected from the group consisting of ischemic stroke, cerebral ischemia and traumatic brain injury, said method comprising administering to said patient a pharmaceutically effective amount of a compound according to claim 1.

13. A method of preparing a compound corresponding to formula I:

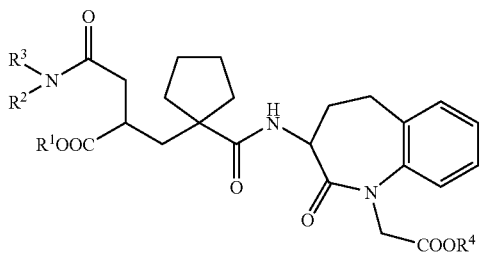

wherein
R¹ is hydrogen or a group forming a biolabile ester,
R² is hydrogen, $C_{1-4}$-alkyl or $C_{1-4}$-hydroxyalkyl, the hydroxyl group of which is optionally esterified with $C_{2-4}$-alkanoyl or an amino acid residue, and
R³ is $C_{1-4}$-alkyl; $C_{1-4}$-alkoxy-$C_{1-4}$-alkyl; $C_{1-4}$-hydroxyalkyl, which is optionally substituted by a second hydroxyl group and the hydroxyl groups of which are each optionally esterified with $C_{2-4}$-alkanoyl or an amino acid; $(C_{0-4}$-alkyl$)_2$amino-$C_{1-6}$-alkyl; $C_{3-7}$-cycloalkyl; $C_{3-7}$-cycloalkyl-$C_{1-4}$-alkyl; phenyl-$C_{1-4}$-alkyl, the phenyl group of which is optionally substituted once or twice by $C_{1-4}$-alkyl, $C_{1-4}$-alkoxy or halogen; naphthyl-$C_{1-4}$-alkyl; $C_{3-6}$-oxoalkyl; phenylcarbonylmethyl, the phenyl group of which is optionally substituted once or twice by $C_{1-4}$-alkyl, $C_{1-4}$-alkoxy or halogen, or 2-oxoazepanyl, or
R² and R³ together are $C_{4-7}$-alkylene, the methylene groups of which are optionally replaced once or twice by carbonyl, nitrogen, oxygen or sulfur and which are optionally substituted once by hydroxy, which in turn is optionally esterified with $C_{2-4}$-alkanoyl or an amino acid; $C_{1-4}$-alkyl; $C_{1-4}$-hydroxyalkyl, the hydroxyl group of which is optionally esterified with $C_{2-4}$-alkanoyl or an amino acid;phenyl or benzyl, and
R⁴ is hydrogen or a group forming a biolabile ester,
or a physiologically acceptable salt thereof;
said method comprising:
reacting a compound corresponding to formula II:

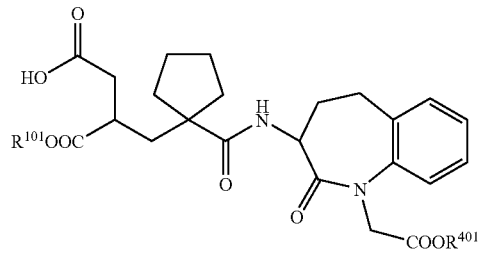

wherein $R^{101}$ and $R^{401}$, independently of each other, are each an acid-protecting group,
with a compound corresponding to formula III:

wherein R² and R³ have the above meanings,
and if R² or R³ contain free hydroxyl groups, optionally reacting the free hydroxyl groups with a compound corresponding to formula IV:

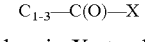

wherein X stands for a leaving group, or
with an amino acid derivative protected by a suitable protective group, and
if at least one of $R^{101}$ and $R^{401}$ is not a desired biolabile ester forming group, or
if at least one of R² and R³ comprises a protective group,
cleaving off such groups to release an acid group, and thereafter converting the acid group to a biolabile ester, and
optionally converting an acid or base of Formula I into a corresponding physiologically acceptable salt, or
optionally coverting a salt of formula I into a corresponding free acid or base.

14. A compound corresponding to formula II:

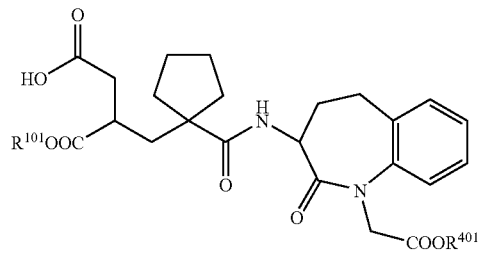

wherein
$R^{101}$ is a carboxylic acid-protecting group and
$R^{401}$ is a carboxylic acid-protecting group.

* * * * *